(12) United States Patent
Nakayama

(10) Patent No.: US 9,995,709 B2
(45) Date of Patent: Jun. 12, 2018

(54) SUBSTRATE MODIFICATION METHOD

(71) Applicant: ARKRAY, Inc., Kyoto (JP)

(72) Inventor: Yusuke Nakayama, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 419 days.

(21) Appl. No.: 13/661,891

(22) Filed: Oct. 26, 2012

(65) Prior Publication Data
US 2013/0105316 A1    May 2, 2013

(30) Foreign Application Priority Data

Oct. 31, 2011 (JP) .................................. 2011-239365
Oct. 17, 2012 (JP) .................................. 2012-230118

(51) Int. Cl.
*G01N 27/447* (2006.01)

(52) U.S. Cl.
CPC ..... *G01N 27/447* (2013.01); *G01N 27/44747* (2013.01)

(58) Field of Classification Search
CPC ...... G01N 30/02; G01N 30/56; G01N 30/203; G01N 2030/567
See application file for complete search history.

(56) References Cited

U.S. PATENT DOCUMENTS

| 7,195,924 B2* | 3/2007 | Hwang | G01N 33/54353 435/4 |
| 7,265,182 B2* | 9/2007 | Lin | C08G 73/10 525/183 |
| 2005/0153350 A1 | 7/2005 | Hwang | |
| 2006/0057209 A1* | 3/2006 | Chapman | B01J 20/28035 424/486 |
| 2009/0200166 A1* | 8/2009 | Nakayama et al. | 204/451 |
| 2010/0258440 A1* | 10/2010 | Sugiyama et al. | 204/451 |

FOREIGN PATENT DOCUMENTS

| CN | 101556248 A | 10/2009 | |
| CN | 101622532 A | 1/2010 | |
| EP | 0452055 A1 | 10/1991 | |
| EP | 2081021   * | 7/2009 | .......... G01N 27/447 |
| EP | 2081021 A1 | 7/2009 | |
| EP | 2144057   * | 1/2010 | .......... G01N 27/447 |
| EP | 2144057 A1 | 1/2010 | |

(Continued)

OTHER PUBLICATIONS

English Translate of Toshinori (JP2003-165867A).*

(Continued)

*Primary Examiner* — Luan V Van
*Assistant Examiner* — Steven Rosenwald
(74) *Attorney, Agent, or Firm* — Morgan, Lewis & Bockius LLP

(57) ABSTRACT

Provided is a substrate modification method that enables improvement of reproducibility in measurement with use of capillary electrophoresis. The substrate modification method includes immobilizing, to a substrate surface, at least two types of modification groups selected from three types of modification groups that are a type of a modification group having one functional group, a type of a modification group having two to nine functional groups, and a type of a modification group having ten or more functional groups.

6 Claims, 5 Drawing Sheets

(56) References Cited

FOREIGN PATENT DOCUMENTS

| JP | 2003-165867 A | 6/2003 |
| JP | 2005-201901 A | 7/2005 |
| JP | 2005-291926 A | 10/2005 |
| JP | 4336970 B | 7/2009 |
| JP | 2011-201740 A | 10/2011 |

OTHER PUBLICATIONS

Gelest, Silane Coupling Agents, 2006.*
Office Action issued in corresponding Chinese Patent Application No. 201210437670.0 dated Jun. 23, 2014.
Kitagawa et al., "Electrophoretic analysis of proteins and enantiomers using capillaries modified by a successive multiple ionic-polymer layer (SMIL) coating technique," Analytical and Bioanalytical Chemistry, 386: 594-601 (2006).
Millot et al., "Overview of the Surface Modification Techniques for the Capillary Electrophoresis of Proteins," Advances in Chromatography, 40: 427-466 (2000).
Liu et al., "Permanent Surface Modification of Polymeric Capillary Electrophoresis Microchips for Protein and Peptide Analysis," Electrophoresis, 27: 3533-3546 (2006).
Katayama et al., "Stable Capillary Coating with Successive Multiple Ionic Polymer Layers," Analytical Chemistry, 70: 2254-2260 (1998).
Katayama et al., "Stable Cationic Capillary Coating with Successive Multiple Ionic Polymer Layers for Capillary Electrophoresis," Analytical Chemistry, 70: 5272-5277 (1998).
Search Report issued in related European Patent Application No. 12190615.0 dated Jan. 30, 2013.
Office Action issued in corresponding European Patent Application No. 12190615.0 dated Apr. 28, 2015.
Office Action issued in corresponding Chinese Patent Application No. 201210437670.0 dated Aug. 5, 2015.
Office Action issued in corresponding European Patent Application No. 12190615.0 dated May 17, 2016.
Office Action issued in corresponding Japanese Patent Application No. 2012-230118 dated Sep. 17, 2013.
Office Action issued in corresponding European Patent Application No. 12190615.0 dated Jun. 2, 2017.

* cited by examiner

SUBSTRATE MODIFICATION METHOD

BACKGROUND OF THE INVENTION

1. Field of the Invention

The present disclosure relates to a substrate modification method, a device manufacturing method, and a device.

2. Description of Related Art

Introduction of functional groups to a substrate surface is used in various fields, for example, junction of substrates, immobilization of biomolecules to a substrate surface, etc. For example, JP2003-165867A discloses a silane coupling agent obtained by causing tetracarboxylic anhydride to react with a silane coupling agent having an amino group so that excellent adhesion of an inorganic-type substrate with a resin that requires high-temperature heating is achieved. JP2005-201901A discloses a method of causing hydrolysis of an anhydride functional group introduced to a substrate surface so as to obtain a carboxyl group, then, causing the carboxyl group to react with carbodiimide and succinimide so as to activate the carboxyl group, and thereafter bringing biomolecules into contact therewith, thereby immobilizing the biomolecules.

Microchip devices have an advantage of reducing a required amount of a reagent and/or a sample, or reducing an analysis time, as compared with conventional analyses. Therefore, microchip devices are used in analysis of various target analytes such as hemoglobin A1c (HbA1c) in blood, AFP and prothrombin as protein in serum, and the like, by using capillary electrophoresis. On the other hand, in the case where separation analysis is carried out by capillary electrophoresis with the use of a microchip device, there is a problem that a sufficiently high resolution cannot be achieved, depending on the material of the substrate of the microchip device and the type of the target analyte. To solve this problem, for example, introduction of a functional group to an inner wall surface of a channel of the microchip device has been proposed. The introduction of a functional group to an inner wall surface of a channel is useful for controlling the occurrence of electroosmotic flow (EOF) in the channel in some cases. JP2005-291926A discloses that a chemical compound having a polar group is chemically bonded to a silanol group on an inner wall surface of a fused silica glass capillary tube so that stable dissociability is imparted to the inner wall surface of the capillary tube.

SUMMARY OF THE INVENTION

The conventional method, however, has a problem in that reproducibility in measurement using capillary electrophoresis is insufficient. There is another problem in that sharpness of separation in the measurement using capillary electrophoresis is insufficient.

The present disclosure, in one aspect, provides a substrate modification method, a device manufacturing method, and a device that enable improvement of reproducibility in measurement with use of capillary electrophoresis. The present disclosure, in another aspect, also provides a substrate modification method, a device manufacturing method, and a device that enable improvement of reproducibility and sharpness of separation in measurement using capillary electrophoresis.

The present disclosure, in one aspect, relates to a substrate modification method that includes immobilizing, to a substrate surface, at least two types of modification groups selected from three types of modification groups that are a type of a modification group having one functional group, a type of a modification group having two to nine functional groups, and a type of a modification group having ten or more functional groups.

The present disclosure, in another aspect, relates to a method for manufacturing a separation analysis device having a channel, wherein at least two types of modification groups selected from three types of modification groups that are a type of a modification group having one functional group, a type of a modification group having two to nine functional groups, and a type of a modification group having ten or more functional groups are immobilized to an inner wall surface of the channel.

The present disclosure, in still another aspect, relates to a separation analysis device having a channel, wherein at least two types of modification groups selected from three types of modification groups that are a type of a modification group having one functional group, a type of a modification group having two to nine functional groups, a type of a modification group having ten or more functional groups are immobilized to an inner wall surface of the channel.

According to the present disclosure, it is possible to provide a substrate modification method, a method for manufacturing a device, and a device that enable improvement of reproducibility in measurement using capillary electrophoresis, as one aspect. According to the present disclosure, it is possible to provide a substrate modification method, a method for manufacturing a device, and a device that enables improvement of reproducibility and sharpness of separation in measurement using capillary electrophoresis, as one aspect.

DETAILED DESCRIPTION OF THE INVENTION

Figure 1A:
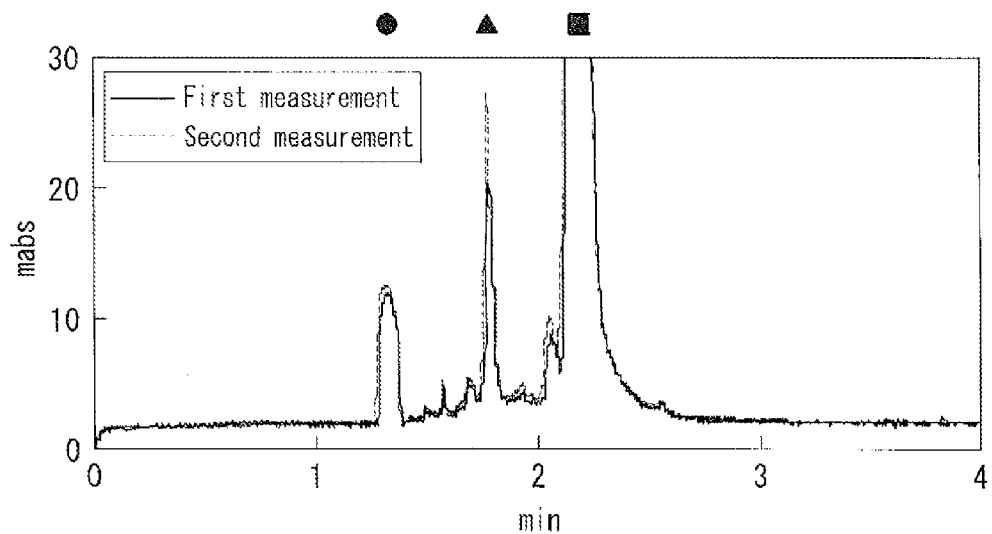
FIGS. 1A and 1B are graphs showing the exemplary results of Example 1.

The phrase of "reproducibility in measurement using capillary electrophoresis is insufficient" described herein refers to variations in measurement results due to differences among measurement operations and/or differences among capillaries, and refers to a phenomenon 1) and/or a phenomenon 2) below, in one or a plurality of embodiments:

1) in the case where measurement using capillary electrophoresis is carried out with use of one and the same capillary channel at least two or more times, peak detection times of respective components and/or EOF in measurement operations have a difference of more than one second, or have a difference of more than 1% of the detection period, in one or a plurality of embodiments;

2) in the case where a plurality of capillary channels and measurement of capillary electrophoresis is carried out using the respective capillary channels, average values of peak detection times of respective components and/or EOF have a difference of more than one second, or have a difference of more than 1% of the detection period, in one or a plurality of embodiments.

The phrase of "sharpness of separation in measurement using capillary electrophoresis is insufficient" described herein refers to that the degree of separation of peaks and/or the peak detection sensitivity is low in one or a plurality of embodiments, and refers to a phenomenon 1) and/or a phenomenon 2) below, in one or a plurality of embodiments:

1) the peak width is wide (the inclination is gradual);

2) a peak of a substance as a target analyte, and a peak of a substance that is present before and/or after the peak of the target analyte come together, and are detected as one peak.

The phrase of "improve sharpness of separation in measurement using capillary electrophoresis" described herein refers to that a degree of separation of peaks and/or detection sensitivity of peaks is high, and refers to a phenomenon 1) and/or a phenomenon 2) below, in one or a plurality of embodiments:

1) the peak width is narrow (the peak is sharp). In one or a plurality of embodiments, the peak width is 2 mm or less, and preferably, 1.8 mm or less. Alternatively, the half value width that is indicative of a width at a point where the height is half of the peak height is 0.9 mm or less, and preferably 0.85 mm or less. It should be noted that the peak width can be calculated in the following manner. In capillary electrophoresis, the migration speed of an object varies with the time when it is detected. Therefore, the "migration speed of the peak" is assumed to be "(separation length)/(peak top detection time)", and the "peak start time" and the "peak end time" are assumed to be the rising and the falling of the peak calculated based on inclinations of a pherogram, respectively. A peak width can be obtained by multiplying the obtained migration speed by the value obtained by subtracting the peak start time from the peak end time. On the other hand, the half value width is obtained by multiplying the migration speed by a time difference between two time points where the height is half of the height of the peak top, the two time points appearing before and after the peak top;

2) a peak of a substance as a target analyte, and a peak of a substance that is present before and/or after the peak of the target analyte, are detected separately. In one or a plurality of embodiments, a peak of hemoglobin A1c and a peak before and/or after a peak of hemoglobin A1c can be detected separately, and/or a peak of hemoglobin A0 and a peak before and/or after a peak of hemoglobin A0 can be detected separately, and/or hemoglobin A1a and hemoglobin A1b can be detected as one peak.

It was found that insufficient reproducibility is due to the state of modification on the inner wall surface of the channel, more specifically, the number of functional groups that modify the inner wall surface of the channel (substrate surface), and/or interstices that occur among functional groups. This is more specifically explained as follows. The number of functional groups immobilized to a surface is usually determined depending on the number of coupling groups for mobilization of the functional groups present on a substrate surface. The methods disclosed in JP2003-165867A and JP 2005-201901A, in which a reaction substance to react with a substrate have two or more functional groups that modify a substrate surface, is capable of immobilizing two or more functional groups per one coupling group present on the substrate surface. This makes it possible to introduce a greater number of functional groups than the number of coupling groups that are present on the substrate surface. On the other hand, since the size of the reaction substance is greater with respect to the size of the coupling group, the reaction substance is not immobilized to a coupling group adjacent to the coupling group to which the reaction substance is immobilized, which causes interstices in the reaction substance. In the method disclosed in JP2005-291926A, a reaction substance having one functional group for modifying a substrate surface is used as an example, but in such a case, only one functional group can be introduced with respect to a coupling group present on the substrate surface. Therefore, in some cases, sufficient functional groups cannot be introduced, or interstices occur in the neighboring reaction substance, depending on intervals of the coupling groups present on the substrate surface. Such interstices in the neighboring reaction substance that occur in this way cause the substrate surface to be exposed. This results in that on the substrate surface, groups that exhibit characteristics different from those of the reaction substance are exposed, since there are carbon hydride, functional groups, and/or silanol that the substrate itself owns, as well as silanol and/or carbon hydride of a silane coupling agent, in one or a plurality of embodiments. The number of functional groups introduced to interstices in the reaction substance and/or the substrate surface could affect reproducibility upon measurement. This was found by the inventor.

In other words, the present disclosure is based on the finding that the reproducibility can be improved by modifying a substrate surface by introducing two or three types of modification groups among three types of modification groups that are a type of a modification group having one functional group (hereinafter also referred to as a "modification group A"), a type of a modification group having two to nine functional groups (hereinafter also referred to as a "modification group B"), and a type of a modification group having ten or more functional groups (hereinafter also referred to as a "modification group C").

Details of the mechanism that the introduction of the above-described modification groups to a substrate surface leads to improvement of reproducibility are not known, but can be presumed as follows. In the case where the modification groups A and the modification groups B are introduced to the substrate surface, an interstice can occur between adjacent ones of the modification groups B, since the modification group B has two or more functional groups. On the other hand, since the number of functional groups possessed by the modification group A is one, the size of the modification group A is smaller as compared with the modification group B. Therefore, the modification group A is immobilized in the interstice that occurs between adjacent ones of the modification groups B. As a result, a sufficient number of functional groups can be introduced to the substrate surface. Besides, the occurrence of interstices among the functional groups can be suppressed, whereby the substrate surface can be modified uniformly. It seems that these prevent adsorption of components in a sample to a substrate surface, and as a result, the reproducibility is improved. The same applies to the case of the combination of the modification groups A and the modification groups C, the case of the combination of the modification groups B and the modification groups C, and the case of the combination of the modification groups A, the modification groups B, and the modification groups C. The present disclosure, however, is not limited to these mechanisms.

The phrase of "immobilizing a modification group" described herein refers to immobilizing a modification group to a substrate surface in a state in which one, two, or more functional groups of the modification group form a covalent bond with another molecule, preferably a molecule on the substrate surface. The covalent bonding is not limited particularly, and examples of the covalent bonding include a Schiff's base formation between an amino group and an aldehyde group, an amide bond between an amino group and a carboxyl group, a copolymerization between double bonds, and an ether bond between a hydroxyl group and an epoxy group, in one or a plurality of embodiments.

[Functional Group]

In one or a plurality of embodiments, the functional group is preferably a polar group, from the viewpoint of interaction with a target analyte and control of the EOF rate. Examples of the polar group, in one or a plurality of embodiments, include a cathodic group (an anionic group) having a negative charge, and an anodic group (a cationic group) having a positive charge. Examples of the cathodic group, in one or a plurality of embodiments, include a carboxyl group, a sulfonic group, a hydroxy group, and silanol group. Examples of the anodic group, in one or a plurality of embodiments, include an amino group and a quaternary ammonium group. The amino group may be any one of a primary amino group, a secondary amino group, or a tertiary amino group. Exemplary preferable polar groups, among the above-described ones, include a carboxyl group, a sulfonic group, and an amino group, from the viewpoint of interaction with a target analyte and control of the EOF rate. In one or a plurality of embodiments in the present disclosure, the control of the EOF rate, for example, uniform increase in the EOF rate, enables electrophoresing a sample within a short time, thereby reducing a measurement time. Particularly, in electrokinetic chromatography in which a pseudo stationary phase moves in a direction opposite to that of the sample, the effect of reducing time while maintaining accuracy can be expected.

In the present disclosure, exemplary combinations of modification groups to be immobilized to a substrate surface include a combination of the modification group A having one function group and the modification group B having two to nine functional groups; a combination of the modification group A having one function group and the modification group C having ten or more functional groups; a combination of the modification group B having two to nine functional groups and the modification group C having ten or more functional groups; and a combination of the modification group A having one functional group, the modification group B having two to nine functional groups, and the modification group C having ten or more functional groups. In one or a plurality of embodiments of the present disclosure, modification groups of one type may be used as each of the modification group A, the modification group B, and the modification group C, or alternatively, modification groups of two or more different types may be used as such.

[Modification Group Having One Functional Group (Modification Group A)]

The phrase of "a modification group having one functional group" described herein refers to a group having one functional group exposed on a substrate surface, and a covalent bond part (hereinafter also referred to as a "bond part") bonded to another molecule (preferably a molecule on the substrate surface). In the modification group A, the functional group exposed on a substrate surface is only one group. Examples of the modification group A, in one or a plurality of embodiments, include, but are not particularly limited to, a group having one of the following groups: a carboxyl group, an amino group, a sulfonic group, a silanol group, a phosphoric group, and a hydroxyl group. Specifically, examples of the modification group A include a group expressed as the formula (I) or (II) shown below:

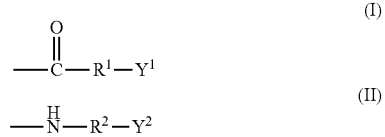

In the formula (I), $R^1$ represents a bond, an alkylene group having 1 to 5 carbon atoms, which may be substituted by a hydroxyl group, an alkenylene group having 2 to 5 carbon atoms, which may be substituted by a hydroxyl group, or a phenylene group. In the formula (II), $R^2$ represents a bond, an alkylene group having 1 to 5 carbon atoms, which may be substituted by a hydroxyl group, an alkenylene group having 2 to 5 carbon atoms, which may be substituted by a hydroxyl group, or a phenylene group. Examples of the alkylene group having 1 to 5 carbon atoms include, but are not particularly limited to, a methylene group, an ethylene group, a trimethylene group, a propane-1,2-diyl group, and a tetramethylene group, in one or a plurality of embodiments. Examples of the alkenylene group having 2 to 5 carbon atoms include, but are not particularly limited to, a vinylene, a propenylene, a butenylene, and a pentenylene, in one or a plurality of embodiments. Examples of $R^1$ and $R^2$ include, but are not particularly limited to, —CH=CH—, —CH$_2$—CH$_2$—, —CH(OH)—CH(OH)—, CH$_2$—, in one or a plurality of embodiments. In the formulae (I) and (II), each of $Y^1$ and $Y^2$ represents a functional group, and preferably represents a carboxyl group, an amino group, a silanol group, a hydroxyl group, a phosphoric group, or a sulfonic group.

In one or a plurality of embodiments, as the modification group A, modification groups of one type may be used, or modification groups of two or more different types may be used in combination. The following groups expressed by the formulae shown below (maleic group, succinic group, fumaric group, tartaric acid, malonic acid, ethylene diamine, etc.) are preferably used as the modification group A.

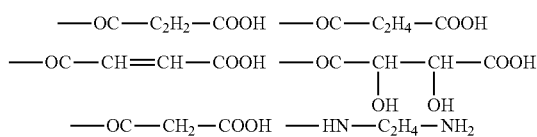

The modification group A has a molecular weight of 45 or more, 74 or more, or alternatively 87 or more, and 324 or less, 253 or less, or alternatively 173 or less, in one or a plurality of embodiments. The modification group A has a molecular weight of 45 to 324, 74 to 253, or 87 to 173, in one or a plurality of embodiments.

[Modification Group Having Two to Nine Functional Groups (Modification Group B)]

The phrase of "a modification group having two to nine functional groups" described herein refers to a group having two or more functional groups exposed on a substrate surface, and a covalent bond part (hereinafter also referred to as a "bond part") bonded to another molecule (preferably a molecule on the substrate surface). In one or a plurality of embodiments in the present disclosure, the functional groups that are exposed on a substrate surface and possessed by the modification group B may be two to nine in number, and may be three, four, five, six, seven, or eight. The functional groups in the modification group B are preferably two to five, or more preferably three to five in number, from the viewpoint of the planar integration density of functional groups on a substrate surface in particular. Examples of the modification group B include, but are not particularly limited to, groups each of which has two or more functional groups selected from the group consisting of a carboxyl group, an amino group, a sulfonic group, a silanol group, a phosphoric group, and a hydroxyl group, in one or a plurality of embodiments. The functional groups in the modification group B may be identical or different. Exemplary combinations of the different functional groups in the modification group B in one or a plurality of embodiments include, though not limited particularly to, a carboxyl group and an amino group; a carboxyl group and a sulfonic group; a carboxyl group and a hydroxyl group; and an amino group and a sulfonic group. Specific examples of the modification group B include, but are not particularly limited to, groups expressed by the formulae (III) to (V) shown below, in one or a plurality of embodiments:

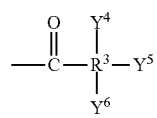 (III)

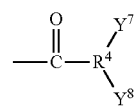 (IV)

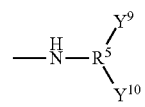 (V)

In the formula (III), $R^3$ represents a tetravalent group of an aromatic compound, and examples of the same include, but are not particularly limited to, groups expressed by the formulae shown below, in one or a plurality of embodiments.

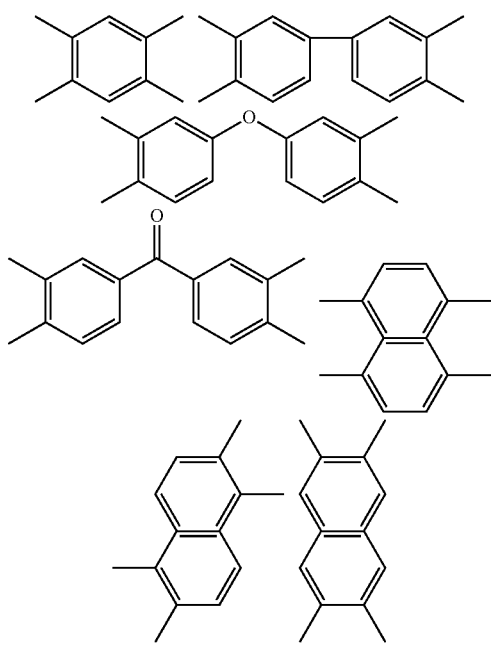

In the formula (III), $Y^4$, $Y^5$, and $Y^6$ independently represent functional groups, respectively, which are preferably a carboxyl group, an amino group, or a sulfonic group. $Y^4$, $Y^5$, and $Y^6$ may be identical or different.

In the formulae (IV) and (V), each of $R^4$ and $R^5$ represents a branched-chain alkylene group having 2 to 6 carbon atoms, or a trivalent group of an aromatic compound. Examples of the trivalent group of an aromatic compound include, but are not particularly limited to, the groups expressed by the formula shown below, in one or a plurality of embodiments.

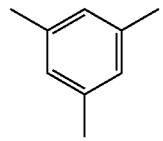

In the formula (IV), $Y^7$ and $Y^8$ independently represent functional groups, respectively, each of which is preferably a carboxyl group, an amino group, or a sulfonic group. $Y^7$ and $Y^8$ may be identical or different. In the formula (V), $Y^9$ and $Y^{10}$ independently represent functional groups, respectively, which are preferably a carboxyl group, an amino group, or a sulfonic group. $Y^9$ and $Y^{10}$ may be identical or different.

As the modification group B, in one or a plurality of embodiments, those of one type may be used, or alternatively, those of two or more different types may be used in combination. Preferably used examples of the modification group B, in one or a plurality of embodiments, include the group expressed by the formula shown below (pyromellitic acid, oxydiphthalic acid, mellitic acid, naphthalene tetracarboxylic acid, etc.).

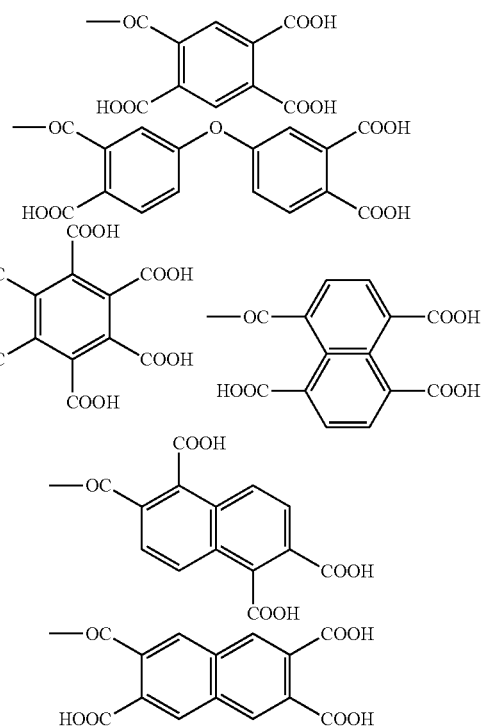

The modification group B, in one or a plurality of embodiments, has a molecular weight of 89 or more, 131 or more, or alternatively 173 or more, and 934 or less, 534 or less, or alternatively 325 or less. The modification group B, in one or a plurality of embodiments, has a molecular weight of 89 to 934, 131 to 534, or 173 to 325.

[Modification Group Having Ten or More Functional Groups (Modification Group C)]

The phrase of "a modification group having ten or more functional groups" described herein refers to a group having ten or more functional groups exposed on a substrate surface, and a covalent bond part (hereinafter referred to as a "bond part") bonded to another molecule (preferably a molecule on the substrate surface). From the viewpoint that the functional groups in the modification group C, particularly those being provided three-dimensionally on a substrate surface, allow the total number of functional groups in the entirety to increase, a polymer substance having many functional groups can be used. The functional groups that are exposed on a substrate surface and possessed by the modification group C may be at least 10 in number, and may be 20 or more, 40 or more, or alternatively 50 or more, and 10,000 or less, 2,000 or less, or alternatively 400 or less. The functional groups that are exposed on a substrate surface and are possessed by the modification group C may be 10 to 10,000, 20 to 2,000, 40 to 400, or 50 to 400, in one or a plurality of embodiments. Examples of the modification group C include, but are not particularly limited to, groups each of which has two or more functional groups selected from the group consisting of a carboxyl group, an amino group, a sulfonic group, a silanol group, a phosphoric group, and a hydroxyl group, in one or a plurality of embodiments. The functional groups in the modification group C may be identical or different. Exemplary combinations of the different functional groups in the modification group C in one or a plurality of embodiments include, though not limited particularly to, a carboxyl group and an amino group; a carboxyl group and a sulfonic group; a carboxyl group and a hydroxyl group; and an amino group and a sulfonic group. The modification group C, in one or a plurality of embodiments, may have a molecular weight of 1,000 or more, preferably 3,000 or more, 5,000 or more, or alternatively 10,000 or more, and 2,500,000 or less, 500,000 or less, or alternatively 100,000 or less. The modification group C, in one or a plurality of embodiments, may have a molecular weight of 1,000 to 2,500,000, 3,000 to 500,000, 5,000 to 100,000, or alternatively 10,000 to 100,000.

Examples of the modification group C include, but are not particularly limited to, a group having a structure which is formed by polymerization of saccharide rings and to which functional groups are bound, or a group having a structure which is formed by polymerization of methyl methacrylate or the like and to which functional groups are bound, in one or a plurality of embodiments. Examples of the group having a structure which is formed by polymerization of saccharide rings and to which functional groups are bound include the groups expressed by the formulae shown below (alginic acid, hyaluronic acid, chondroitin sulfate A, chondroitin sulfate B, chondroitin sulfate C), and heparin, in one or a plurality of embodiments.

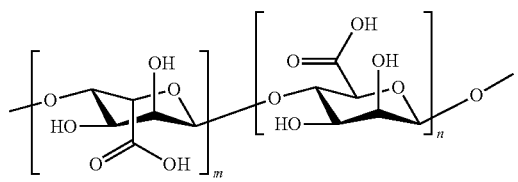

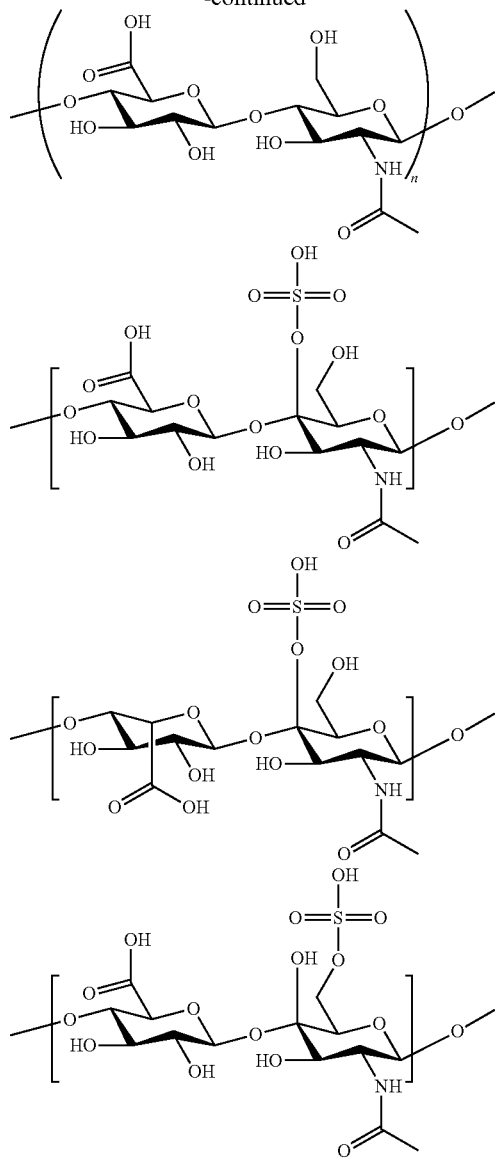

Examples of the group having a structure which is formed by polymerization of ethylene, methylene methacrylate, or the like and to which functional groups are bound include polymaleic acid, polyacrylic acid, and polymaleic acid-polymethacrylic acid copolymer, in one or a plurality of embodiments.

The combination of the modification group A and the modification group B can be decided appropriately depending on the application purpose of the modified substrate, the type of the substrate, and the like. The modification group A in combination may be selected depending on the number of the functional group of the modification group B, the molecular weight thereof, or the like. Examples of the combination of the modification group A and the modification group B include, but are not particularly limited to, the combination of a group expressed by the formula (I) and a group expressed by the formula (III), in one or a plurality of embodiments. The following examples (1) to (3) ((1) succinic acid and pyromellitic acid, (2) maleic acid and pyromellitic acid, and (3) succinic acid and naphthalene tetracarboxylic acid) can be used, and the combination (1) (succinic acid and pyromellitic acid) is preferable as the combination of the group expressed by the formula (I) and the group expressed by the formula (III), from the viewpoint of the molecular size and the number of functional groups of the reaction substance, in one or a plurality of embodiments. It should be noted that the combination of the modification group A and the modification group B in the present disclosure is not limited to these.

| A | B |
|---|---|
| (1) —OC—C₂H₄—COOH | |
| (2) —OC—C₂H₂—COOH | |
| (3) —OC—C₂H₄—COOH | |

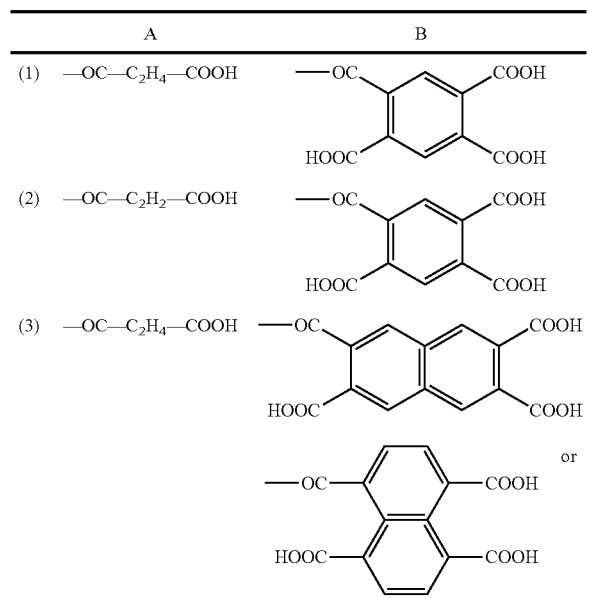

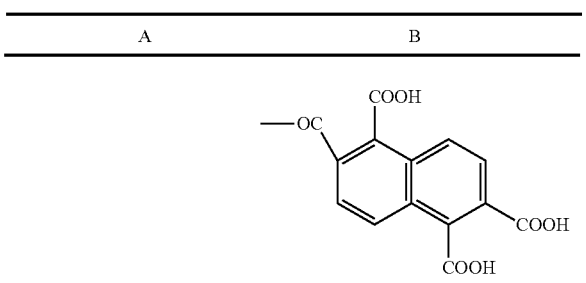

The combination of the modification group C and the modification group A, or the combination of the modification group C and the modification group B can be decided appropriately depending on the application purpose of the modified substrate, the type of the substrate, and the like. The modification group A or the modification group B to be combined with the modification group C may be selected depending on the number of the functional group of the modification group C, the molecular weight thereof, or the like. Examples of the combination of the modification group C and the modification group A include, but are not particularly limited to, the combination of chondroitin sulfate and succinic acid (the combination expressed by the formula (4) shown below), the combination of chondroitin sulfate and maleic acid (the combination expressed by the formula (5) shown below), the combination of polymaleic acid and succinic acid, the combination of heparin and succinic acid, the combination of heparin and malonic acid, in one or a plurality of embodiments. It should be noted that the combination of the modification group C and the modification group A in the present disclosure is not limited to these.

| A | C |
|---|---|
| (4) —OC—C₂H₄—COOH | |

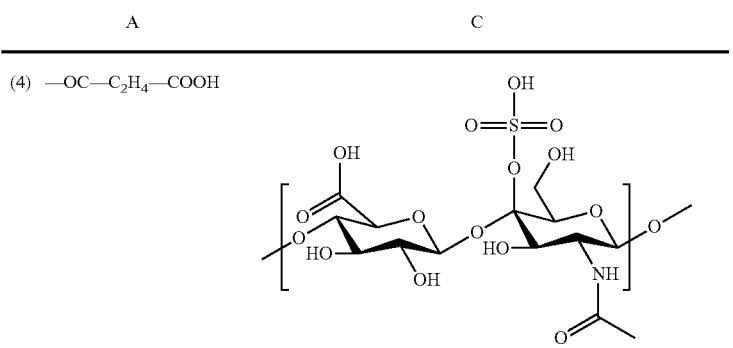

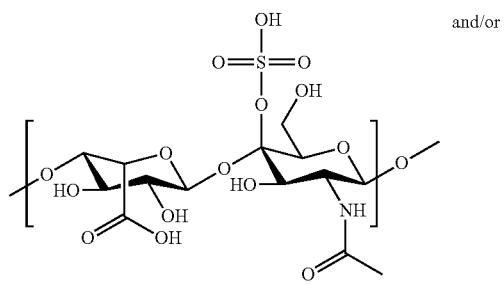

| A | C |
|---|---|

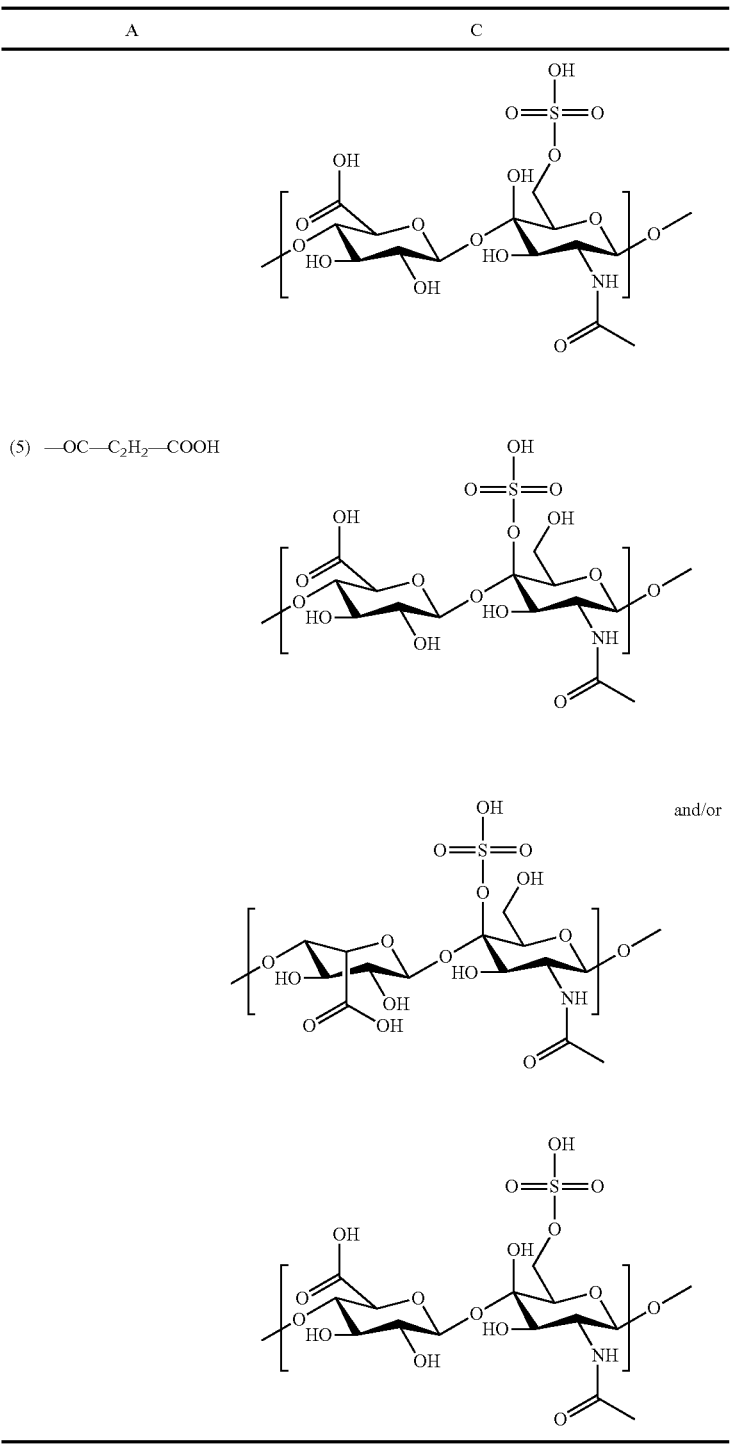

Examples of the combination of the modification group C and the modification group B include, but are not particularly limited to, the combination of chondroitin sulfate and pyromellitic acid (the combination expressed by the formula (6) shown below), the combination of heparin and mellitic acid, the combination of chondroitin sulfate and naphthalene tetracarboxylic acid (the combination expressed by the formula (7) shown below), in one or a plurality of embodiments. The combination of the modification group C and the modification group B is particularly effective in the case where the modification group C has a structure which is formed by polymerization of saccharide rings and to which functional groups are bound to, since the modification group C in this case has a large three-dimensional structure. It should be noted that the combination of the modification group C and the modification group B in the present disclosure is not limited to these.

| B | C |
|---|---|
| 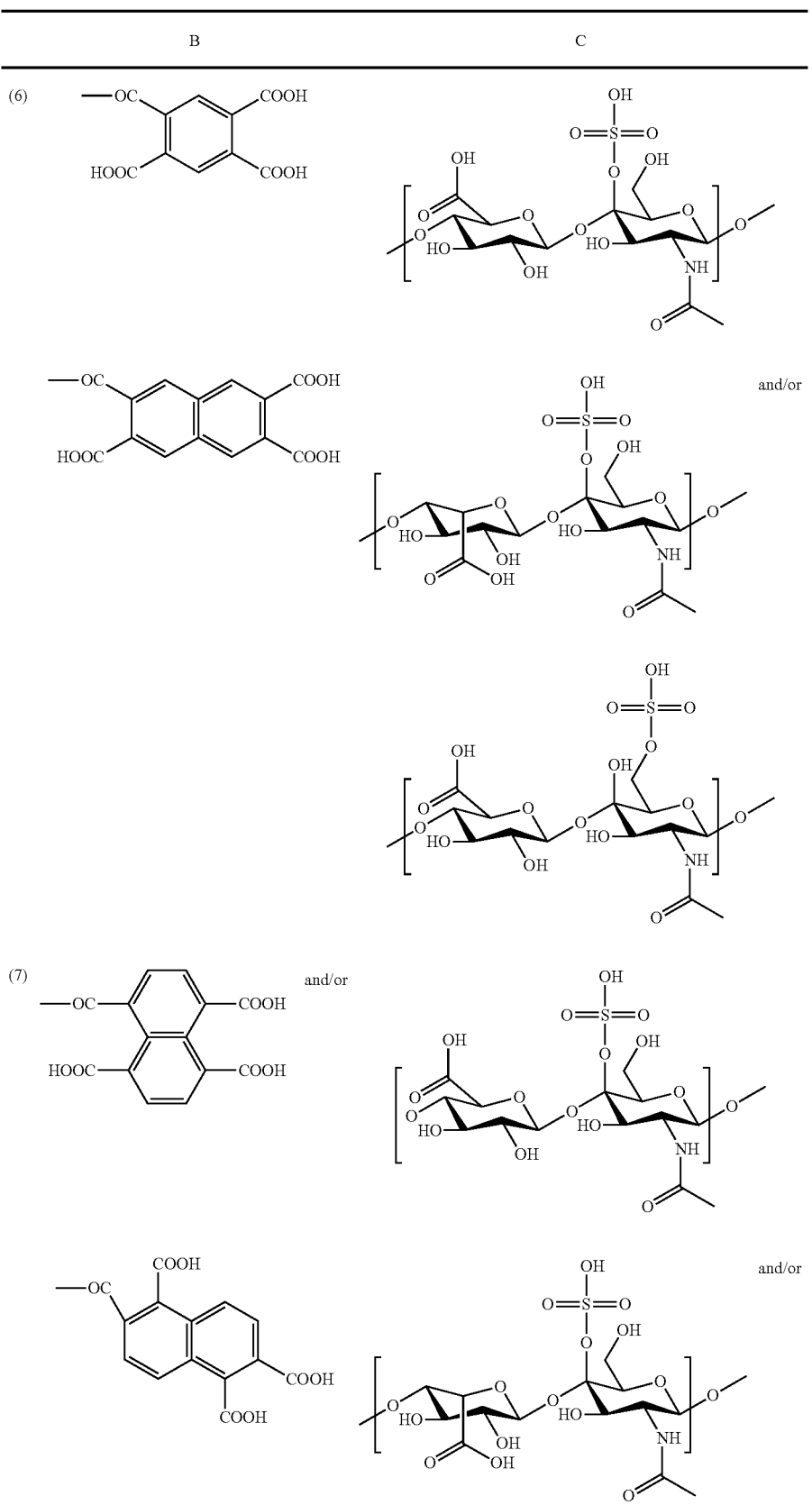 | |

| B | C |
|---|---|
| | 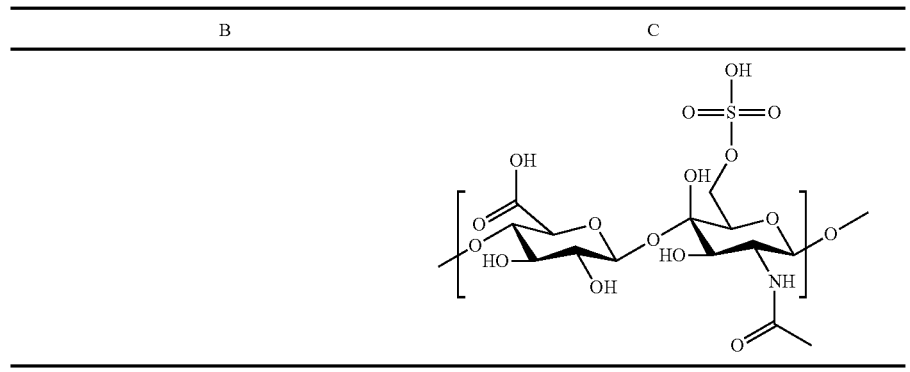 |

[Substrate]

An inorganic material or an organic material can be used as a substrate material, and the substrate material is not limited particularly. Examples of the substrate material include resins, quartz, and glass. Among these, resins are preferred, from the viewpoint of handleability and low costs. Among resins, those which are formed into channels easily and are not deformed easily are preferred, for example, thermoplastic resins. Among thermoplastic resins, the following are preferred from the viewpoint of being formed into channels easily and being not easily deformed: acrylic resins such as methyl polymethacrylate (PMMA); polymethyl methacrylate; polycarbonate; polyvinylidene chloride; cyclic polyolefin; polyether ether ketone; polystyrene; and polytetrafluoroethylene (PTFE). Among these, methyl polymethacrylate is more preferred. The shape of the substrate is not limited particularly, and the substrate may be in a plate form, or a tube form.

[Substrate Modification Method]

The present invention, in one aspect, relates to a substrate modification method that includes immobilizing, to a substrate surface, at least two types of modification groups selected from three types of modification groups that are a type of a modification group (modification group A) having one functional group, a type of a modification group (modification group B) having two to nine functional groups, and a type of a modification group (modification group C) having ten or more functional groups (hereinafter also referred to as the "modification method of the present disclosure"). With the modification method of the present invention, it is possible to provide a substrate that allows reproducibility in measurement with use of capillary electrophoresis to be improved, in one or a plurality of embodiments. Further, with the modification method of the present invention, it is possible to achieve an effect of improving sharpness of separation in measurement with use of capillary electrophoresis, in one or a plurality of embodiments.

In one or a plurality of embodiments, the immobilization of the modification groups to a substrate surface can be performed by bringing at least two types of compounds selected from the following three types of compounds into contact with a substrate surface: a compound A having two functional groups; a compound B having three to ten functional groups; and a compound C having eleven or more functional groups. The contact of compounds can be achieved by application, immersion, dropping, atomization, or the like in one or a plurality of embodiments.

In the case where the modification group A and the modification group B are immobilized to a substrate surface, the immobilization of the modification group A and the modification group B to the substrate surface can be carried out by bringing the compound A having two functional groups and the compound B having three or more functional groups into contact with the substrate surface in one or a plurality of embodiments. The contact of compounds A and B can be achieved by, for example, application, immersion, dropping, atomization, or the like. The order in which the compound A and the compound B are brought into contact with the substrate surface is not limited particularly. In one or a plurality of embodiments, a mixture of the compound A and the compound B is brought into contact with the substrate surface so that the compounds A and B are brought into contact simultaneously, or alternatively, the compound A and the compound B may be brought into contact with the substrate surface separately. From the viewpoint of suppressing the occurrence of interstices between functional groups and efficiently immobilizing functional groups, it is preferable to bring the compound B into contact with the substrate surface, and thereafter bring the compound A into contact with the substrate surface.

In the case where the modification group A, the modification group B, and the modification group C are immobilized to a substrate surface, the immobilization of the modification group A, the modification group B, and the modification group C to the substrate surface can be carried out by bringing the compound A having two functional groups, the compound B having three to ten functional groups, and the compound C having eleven or more functional groups into contact with the substrate surface, in or a plurality of embodiments. The contact of compounds A, B, and C can be achieved by, for example, application, immersion, dropping, atomization, or the like. The order in which the compound A, the compound B, and the compound C are brought into contact with the substrate surface is not limited particularly. A mixture of the compound A and the compound C, a mixture of the compound B and the compound C, or a mixture of the compound A, the compound B, and the compound C is brought into contact with the substrate surface so that the compounds A and C, the compounds B and C, or the compounds A, B, and C are brought into contact simultaneously, respectively. Alternatively, the compound A, the compound B, and the compound C may be brought into contact with the substrate surface separately. From the viewpoint of suppressing the occurrence of interstices among functional groups and efficiently immobilizing functional groups, it is preferable to bring the compound C into contact with the substrate surface, and thereafter bring the compound A and the compound B into contact with the substrate surface.

The compound A is a compound that has two functional groups and that is intended to introduce the modification group A to a substrate surface, and is preferably a compound that has one functional group to function as a part of the modification group and another functional group to be bound to the substrate surface. As the functional group to function as a part of the modification group, the above-described functional group can be used, and examples of the same include a carboxyl group, an amino group, a sulfonic group, a hydroxyl group, and a silanol group in one or a plurality of embodiments. Examples of the functional group to be bound to the substrate surface include a carboxyl group, an amino group, and a hydroxyl group in one or a plurality of embodiments. The number of the functional group to be bound to the substrate surface is not limited particularly, and in one or a plurality of embodiments, the number is one, two, or more, and is preferably one. Examples of the compound A, in one or a plurality of embodiments, include a compound having two carboxyl groups; a compound having one carboxyl group and one amino group; a compound having one carboxyl group and one sulfonic group; a compound having one carboxyl group and one hydroxyl group; a compound having two amino groups; and a compound having one amino group and one sulfonic group. Specific examples of the compound A, in one or a plurality of embodiments, include, but are not particularly limited to, dicarboxylic acid, monoaminocarboxylic acid, diamine, and monoaminosulfonic acid. Examples of the dicarboxylic acid include succinic acid, glutaric acid, and maleic acid, in one or a plurality of embodiments. Dicarboxylic acid may be an anhydride. Examples of the anhydride of dicarboxylic acid include succinic anhydride, glutaric anhydride, and maleic anhydride, in one or a plurality of embodiments. Examples of monoaminocarboxylic acid include 4-aminobenzoic acid, and glycine in one or a plurality of embodiments. Examples of diamine include ethylene diamine, in one or a plurality of embodiments. Examples of monoaminosulfonic acid include amidosulfonic acid and taurine, in one or a plurality of embodiments. The compound A is preferably maleic acid, succinic acid, ethylene diamine, or the like, from the viewpoint of the molecular size of the modification group A to be introduced to the substrate surface, and the improvement of reproducibility. As the compound A, one type of the compound may be used, or two or more different types of the compounds may be used in combination.

The compound A has a molecular weight of 46 or more, 75 or more, 95 or more, or alternatively 104 or more, and 340 or less, 270 or less, or alternatively 190 or less, in one or a plurality of embodiments. The compound A has a molecular weight of 46 to 340, 75 to 270, 95 to 190, or 104 to 190, in one or a plurality of embodiments.

The compound B is a compound that has at least three to ten functional groups and that is intended to introduce the modification group B onto a substrate surface, and is preferably a compound that has two to nine functional groups to function as a part of the modification group and another functional group(s) to be bound to the substrate surface. Examples of the functional group to function as a part of the modification group, and examples of the functional group to be bound to a substrate surface include the same functional groups as those of the compound A in one or a plurality of embodiments. The number of functional groups to be bound to a substrate surface is the same as that of the compound A in one or a plurality of embodiments. Examples of the compound B, in one or a plurality of embodiments, include a compound having three or four to nine carboxyl groups; a compound having two or more carboxyl groups and one or more amino groups; a compound having one or more carboxyl groups and two or more sulfonic groups; a compound having one or more carboxyl groups and two or more hydroxyl groups; and a compound having one or more amino groups and two or more sulfonic groups. Specific examples of the compound B, in one or a plurality of embodiments, include, but are not particularly limited to, tetracarboxylic acids, hexacarboxylic acids, and disulfobenzoic acids. Examples of the tetracarboxylic acid, in one or a plurality of embodiments, include pyromellitic acid, oxydiphthalic acid, mellitic acid, 3,3',4,4'-benzophenone tetracarboxylic acid, 3,3',4,4'-biphenyl tetracarboxylic acid, 1,2,5,6-naphthalene tetracarboxylic acid, 2,3,6,7-naphthalene tetracarboxylic acid, 1,4,5,8-naphthalene tetracarboxylic acid, 2,3,5,6-pyridine tetracarboxylic acid, 3,4,9,10-perylene tetracarboxylic acid, sulfonyldiphthalic acid, m-terphenyl-3,3',4,4'-tetracarboxylic acid, p-terphenyl-3,3'4,4'-tetracarboxylic acid, 1,1,1,3,3,3-hexafluoro-2,2-bis(2,3- or 3,4-dicarboxyphenyl)propane, 2,2-bis(2,3- or 3,4-dicarboxyphenyl)propane, 2,2-bis[4'-(2,3- or 3,4-dicarboxyphenoxy)phenyl]propane, and 1,1,1,3,3,3-hexafluoro-2,2-bis[4'(2,3- or 3,4-dicarboxyphenoxy)phenyl]propane. Tetracarboxylic acid may be an anhydride. Examples of the anhydride of tetracarboxylic acid include pyromellitic dianhydride, and oxydiphthalic acid, in one or a plurality of embodiments. Examples of hexacarboxylic acid include mellitic acid, and 1,2,3,4,5,6-cyclohexane hexacarboxylic acid, in one or a plurality of embodiments. Hexacarboxylic acid may be an anhydride, and examples of the anhydride of hexacarboxylic acid include mellitic anhydride, one or a plurality of embodiments. Examples of monoaminodicarboxylic acid include 5-aminoisophthalic acid, glutamic acid, and asparagine acid, in one or a plurality of embodiments. Examples of disulfobenzoic acid include 3,5-disulfobenzoic acid, in one or a plurality of embodiments. As the compound B, tetracarboxylic acid is preferred from the viewpoint of the molecular size of the modification group B to be introduced to a substrate surface and the improvement of reproducibility, though it is not limited to this, and pyromellitic acid, oxydiphthalic acid, naphthalene tetracarboxylic acid, and the like are preferred more, in one or a plurality of embodiments. As the compound B, one type of the compound may be used, or two or more different types of the compounds may be used in combination, in one or a plurality of embodiments.

The compound B has a molecular weight of 90 or more, 150 or more, or alternatively 190 or more, and 950 or less, 550 or less, or alternatively 342 or less, in one or a plurality of embodiments. The compound B has a molecular weight of 90 to 950, 150 to 550, or 190 to 342, in one or a plurality of embodiments.

The compound C is a compound that has at least ten or more functional groups and that is intended to introduce the modification group C to a substrate surface, and is preferably a compound that has nine or more functional groups to function as a part of the modification group and another functional group(s) to be bound to the substrate surface. Examples of the functional group to function as a part of the modification group, and examples of the functional group to be bound to a substrate surface include the same functional groups as those of the compound A. Examples of the compound C include a compound having ten or more carboxyl groups; a compound having ten or more sulfonic groups; and a compound having five or more carboxylic groups and five or more sulfonic group. Specific examples of the compound C, in one or a plurality of embodiments, include, but are not particularly limited to, alginic acid, polyacrylic acid, chondroitin sulfate A, chondroitin sulfate B, chondroitin sulfate C, chondroitin sulfate D, chondroitin sulfate E, hyaluronic acid, heparin, polymaleic acid, and polyacrylic acid.

The compound C has a molecular weight of 3,000 or more, 5,000 or more, or alternatively 10,000 or more, and 2,500,000 or less, 500,000 or less, or alternatively 100,000 or less, in one or a plurality of embodiments. The compound C has a molecular weight of 3,000 to 2,500,000, 5,000 to 500,000, or 10,000 to 100,000, in one or a plurality of embodiments.

The combination of the compound A and the compound B can be decided appropriately depending on the application purpose of the modified substrate, the type of the material of the substrate, etc., in one or a plurality of embodiments. Examples of the combination of the compound A and the compound B include, but are not limited to, the combination of maleic acid and pyromellitic acid, and the combination of succinic acid and naphthalene tetracarboxylic acid, in one or a plurality of embodiments, among which the combination of succinic acid and pyromellitic acid is preferred from the viewpoint of the molecular size and the number of functional groups of the reaction substance. The compound A can be decided appropriately depending on the number of functional groups of the compound B and the molecular weight of the compound B, for example. The molecular weight of the compound A is preferably ½ or less, or more preferably ¼ or less, of the molecular weight of the compound B, from the viewpoint of further reducing interstices among functional groups that could occur on a substrate surface. From the same viewpoint, the compound B preferably has a molecular occupation area greater than, for example, that of an anchor compound present on a substrate surface, or more preferably a molecular occupation area twice or more than that of an anchor compound. The molecular occupation area of the compound B and the anchor compound can be measured by surface elemental analysis, and an angle of contact.

From the viewpoint of the integration density of functional groups on an obtained substrate, it is preferable that pyromellitic acid is used as the compound B and succinic acid is used as the compound A, in one or a plurality of embodiments.

In the case where the compound A and the compound B are brought into contact with a substrate simultaneously, the ratio of the compound A and the compound B can be decided appropriately according to the molecular weights of the compounds A and B, the number of functional groups of the compound B, etc. The ratio of the compound A and the compound B (compound A/compound B, molar ratio) is 1/10 or more, 1/5 or more, or alternatively, 1/3 or more, and 10/1 or less, 4/1 or less, or alternatively, 1/1 or less, in one or a plurality of embodiments, though it is not limited particularly. The ratio of the compound A and the compound B (compound A compound B, molar ratio) is 1:10 to 10:1, preferably 1:5 to 4:1, and more preferably 1:3 to 1:1, in one or a plurality of embodiments.

The combination of the compound A and the compound C, or the combination of the compound B and the compound C can be decided appropriately depending on, for example, the application purpose of the modified substrate, the type of the substrate, and the like. The compound A can be decided appropriately depending on, for example, the number of functional groups of the compound C and/or the molecular weight of the compound C, etc. From the viewpoint of further reducing interstices among functional groups that could occur on a substrate surface, the molecular weight of the compound A is preferably one time or less than that of a molecular weight of a monomer of the compound C (the "monomer" refers to a saccharide including a functional group in the case of a polymer of saccharide, or maleic acid in the case of polymaleic acid), and more preferably 0.6 time or less than that. From the viewpoint of further reducing interstices among functional groups that could occur on a substrate surface, the molecular weight of the compound C is preferably 1.5 times or less than that of a molecular weight of a monomer of the compound C (the "monomer" refers to a saccharide including a functional group in the case of a polymer of saccharide, or maleic acid in the case of polymaleic acid), and more preferably 1.0 time or less than that.

In the modification method of the present disclosure, a functional group for immobilizing a modification group to a substrate surface (hereinafter also referred to as an "functional group for immobilization") is preferably introduced to a substrate surface to which a modification group is immobilized, in one or a plurality of embodiments, and the substrate surface is more preferably treated with an anchor compound. Examples of the functional group for immobilization include an amino group, a vinyl group, a carboxyl group, a methoxy group, an aldehyde group, an epoxy group, and a hydroxyl group, in one or a plurality of embodiments.

Examples of the anchor compound include a silane coupling agent, and polysilazane, in one or a plurality of embodiments, among which a silane coupling agent is preferable from the viewpoint of general versatility. Examples of the silane coupling agent include an amino silane compound, an epoxy silane compound, a vinyl silane compound, and a carboxysilane compound, in one or a plurality of embodiments, among which an amino silane compound is preferred form the handleability.

Examples of the amino silane compound include 3-aminopropyl triethoxy silane; 3-aminopropyltrimethoxy silane; 2-aminoethyl-3-aminopropylmethyl dimethoxy silane; 2-aminoethyl-3-aminopropyltrimethoxy silane; N-2-(aminoethyl)-3-aminopropyltriethoxy silane; N-2-(aminoethyl)-3-aminopropyltrimethoxy silane; tris(dimethylamino)chlorosilane; and tris(dimethylamino)silane. Examples of the vinyl silane compound include vinyl triethoxy silane; vinyl methoxy silane; vinyl tris(2-methoxyethoxy)silane; and vinyl(trifluoromethyl)dimethyl silane. Examples of the carboxysilane compound include p-methyldimethoxysilylethyl benzoic acid trimethylsilyl ester, and trimethylsilyl p-dimethylethoxysilyl ethyl benzoate, as described in JP4336970B.

As another method, for example, the following method can be used for introducing a functional group for immobilization to a substrate surface, in the case where the substrate is made of an acrylic resin such as methyl polymethacrylate. Examples of the method, in one or a plurality of embodiments, include nucleophilic addition-elimination reaction of a primary or secondary amine compound with an acyl group of a methacrylic acid; conversion of a methacrylic acid group possessed by methyl polymethacrylate or the like into a carboxyl group by strong alkali treatment applied to the substrate surface; and conversion of a methyl group possessed by an acrylic resin, or the like, into a carboxyl group by treatment of a substrate surface with VUV (vacuum ultraviolet rays), plasma, or the like. Examples of the primary or secondary amine compound suitable for introduction of an amino group used in the nucleophilic addition-elimination reaction of a primary or secondary amine compound, in one or a plurality of embodiments, include 1,2- diaminopropane, 1,3-diaminopropane, 1,3-diamino-2-propanol, and diaminopyridine. Examples of the primary or secondary amine compound suitable for introduction of a vinyl group used therein include acrylamide. Examples of the primary or secondary amine compound suitable for introduction of a carboxyl group used therein include 4-amino-benzoic acid, 3-amino-benzoic acid, and 3-amino-isobutylic acid.

In the modification method of the present disclosure, in one or a plurality of embodiments, the above-described treatment for introducing a functional group for immobilization to a substrate surface may be carried out prior to the immobilization of a modification group. The introduction of a functional group for immobilization can be decided appropriately depending on the material of the substrate.

The modification method of the present disclosure makes it possible to provide a substrate that enables improvement of reproducibility in the measurement with use of capillary electrophoresis, in one or a plurality of embodiments. According to the present disclosure, it is possible to provide an analysis tool, or a separation analysis device such as an analysis chip, in one or a plurality of embodiments.

[Device Manufacturing Method]

The present disclosure, in another aspect, relates to a method for manufacturing a separation analysis device having a channel, wherein at least two types of modification groups selected from three types of modification groups that are a type of a modification group having one functional group (modification group A), a type of a modification group having two to nine functional groups (modification group B), a type of a modification group having ten or more functional groups (modification group C) are immobilized to an inner wall surface of the channel (hereinafter this method is referred to also as a "manufacturing method of the present disclosure"). According to the manufacturing method of the present disclosure, it is possible to provide a device that enables improvement of reproducibility in measurement with use of capillary electrophoresis, in one or a plurality of embodiments. With the manufacturing method of the present disclosure, it is possible to achieve an effect of providing a device that enables improvement of sharpness of separation in measurement with use of capillary electrophoresis, in one or a plurality of embodiments.

The term of "device" described herein refers to a separation analysis device having a channel, preferably, for example, a capillary tube, an electrophoresis chip, or the like used in separation analysis such as capillary electrophoresis, or capillary electrochromatography.

In the method for manufacturing a device in the present disclosure, the immobilization of a modification group can be performed by the modification method of the present disclosure and a known method for modifying a channel.

[Device]

The present disclosure, in still another aspect, relates to a separation analysis device having a channel, wherein at least two types of modification groups selected from three types of modification groups that are a type of a modification group having one functional group (modification group A), a type of a modification group having two to nine functional groups (modification group B), a type of a modification group having ten or more functional groups (modification group C) are immobilized to an inner wall surface of the channel (hereinafter this separation analysis device is referred to also as a "device of the present disclosure"). The device of the present disclosure may be a device obtained by the device manufacturing method of the present disclosure. The number of functional groups in a modification group immobilized to an inner wall surface of a channel (functional groups exposed on an inner wall surface of a channel) can be measured by, for example, surface elemental analysis, a method of binding a labeling material such as a fluorescent material or a labeling enzyme that is specifically bound to a functional group, or a method of decomposing and extracting a compound including a modification group with alkali or acid and quantifying the same.

In the device of the present disclosure, the modification group having one functional group (modification group A), the modification group having two to nine functional groups (modification group B), and the modification group having ten or more functional groups (modification group C) are preferably immobilized to the channel inner wall via an anchor compound. Examples of the anchor compound are as described above, among which the silane coupling agent is preferred.

The device of the present disclosure, as having a channel, can be used as a sample analyzer, an analysis tool, or an analysis chip, in one or a plurality of embodiments. The device of the present disclosure can be used as a device, a tool, or a chip that allows operations such as mixing, extraction, or phase separation, or chemical reaction to be carried out, and allows a substance to be generated as required, in one or a plurality of embodiments. The device of the present disclosure can be used for separation analysis of a sample in one embodiment, or more specifically, the device of the present disclosure can be used as a microchip of capillary electrophoresis, or a capillary tube for capillary electrophoresis or electrochromatography.

In the case where the device is a capillary tube, its inner diameter is not limited particularly, but it is 10 to 200 μm, or 25 to 100 μm in one or a plurality of embodiments. The capillary tube has a length of 10 to 1000 mm in one or a plurality of embodiments.

In the case where the device is a microchip, its form is not limited particularly, but an exemplary form is as follows, in one or a plurality of embodiments: the device includes two substrates joined, and a recess is formed on at least one of opposed surfaces of the two substrates, whereby the channel is formed. In this form, the two substrates used may be made of different materials. For example, examples of the combination of the materials include a combination of an inorganic material and an organic material, and a combination of different organic materials. The combination of an inorganic material and an organic material is not limited particularly, but examples of the same include a combination of a quartz material and a thermoplastic resin. The combination of different organic materials is not limited particularly, but examples of the same include a combination of an acrylic resin and a cyclic polyolefin, in one or a plurality of embodiments. The size of the device is not limited particularly, but in one or a plurality of embodiments, the length of one side is, for example, 10 to 200 mm, and the thickness is, for example, 0.3 to 5 mm. The dimensions, length, and shape of the channel are not limited particularly. In one or a plurality of embodiments, the diameter of a circumscribed circle of the cross-section of the channel is, for example, 28 to 280 μm, and generally, 35 to 140 μm. The shape of the cross-section of the channel may be rectangular, semicircular, trapezoidal, circular, or elliptical. The shape of the channel is not limited to a linear shape, but may be arbitrarily determined, for example, a shape having a branch at an end, or the like. The shape may be a cross-like shape, a T-letter shape, a Y-letter shape, an X-letter shape, or the like, or may be in a shape obtained by combining some of the same.

[Kit for Modifying Substrate]

The present disclosure, in still another aspect, relates to a kit for modifying a substrate, the kit including at least two types of compounds from three types of compounds, and an instruction manual that explains a method for modifying a substrate surface by the modification method of the present disclosure, the three types of compounds being a compound A having a modification group having one functional group and a group(s) to be bound to a substrate, a compound B having a modification group having two to nine functional groups and a group(s) to be bound to a substrate, and a compound C having a modification group having ten or more functional groups and a group(s) to be bound to a substrate (this kit is hereinafter also referred to as a "kit of the present disclosure"). It should be noted that regarding the kit of the present disclosure, the present disclosure encompasses a case where the instruction manual is not enclosed in the kit for analysis of the present disclosure but is provided on web site.

[Electrophoresis Method]

The present disclosure, in still another aspect, relates to a method of performing capillary electrophoresis with use of the device of the present disclosure (hereinafter this method is also referred to as an "electrophoresis method of the present disclosure"). The phrase of "performing capillary electrophoresis" described herein refers to separating a sample by capillary electrophoresis or capillary electrochromatography. With the electrophoresis method of the present disclosure, which uses the device of the present disclosure, a sample can be separated at excellent sharpness of separation.

The electrophoresis method of the present disclosure may include separating and analyzing a sample. The sample is not limited particularly, and may be, for example, a sample prepared from a sample material, or the sample material itself. The sample material is not limited particularly, and examples of the sample material include a sample of an aqueous solution, a biological sample, and food, in one or a plurality of embodiments. The biological sample is not limited particularly, and examples of the biosample, in one or a plurality of embodiments, include blood; substances derived from blood containing components in blood; culture solutions of fungi, etc.; and extracts of plants, etc. Examples of the components in blood include serum, plasma, erythrocytes, leukocytes, platelets, and the like, in one or a plurality of embodiments. Examples of the blood include blood sampled from a living body. The substance derived from blood that contains erythrocytes is, for example, a substance that is separated from blood or prepared from blood and that contains erythrocytes, in one or a plurality of embodiments, and examples of the same include a blood cell fraction from which plasma is removed, a blood cell concentration, freeze-dried blood, freeze-dried blood cells, hemolyzed samples obtained by hemolyzing whole blood, centrifuged blood, blood samples obtained through spontaneous sedimentation, and washed blood cells. The target analyte is not limited particularly, and in one or a plurality of embodiments, the examples include: a nucleotide chain (e.g., oligonucleotide chain, polynucleotide chain); chromosome; a peptide chain (e.g., C-peptide, angiotensin I, and the like); a protein (e.g., hemoglobin, hemoglobin A1c, immunoglobulin A, immunoglobulin E, immunoglobulin G, immunoglobulin M, albumin, decomposition products thereof, and the like); an enzyme (e.g., amylase, alkaline phosphatase, γ-glutamyl transferase, lipase, creatine kinase, lactate dehydrogenase, glutamate oxaloacetate transaminase, glutamate pyruvate transaminase); bacteria (e.g., Mycobacterium tuberculosis, Streptococcus pneumoniae, staphylococcus, Escherichia coli, Helicobacter pylori, and the like); viruses (e.g., herpesvirus, influenza virus, adenovirus, enterovirus, HBV, HCV, HIV and the like); fungus (e.g., Candida, Cryptococcus and the like); protein or peptide or carbohydrate antigen derived from microorganism; various allergens that cause allergy (e.g., house dust; mite; pollens of Japanese cedar, cypress, bitterweed and the like; and allergens derived from animals such as lobster/shrimp and crab, foods such as egg white, fungus, insects, medicine, chemical substances, and the like); lipid (e.g., lipoprotein and the like); tumor marker protein antigen (e.g., PSA, PGI and the like); sugar chain antigen (e.g., AFP, hCG, transferrin, IgG, thyroglobulin, CA19-9, prostate gland specific antigen, tumor marker sugar chain antigen having a special sugar chain produced by cancer cells, and the like); sugar chains (e.g., hyaluronic acid, β-glucan, sugar chain possessed by for example the above-mentioned sugar chain antigen or the like); hormones (e.g., T3, T4, TSH, insulin, LH, and the like); and chemical substances (e.g., endocrine disruptors such as nonyl phenol, 4-octyl phenol, benzophenone, and the like).

Hereinafter, a stator of the present disclosure will be described in detail using preferred embodiments. For the interpretation, however, the present disclosure is not limited to Embodiments shown below.

Embodiment 1

The following description explains Embodiment 1 as one embodiment of the substrate modification method of the present disclosure, by referring to an example in which the substrate forms an inner wall of a channel of a device, and the modification group B is introduced to a surface of the inner wall first, then the modification group A is introduced.

First, a device having a channel is prepared. A commercially-available device may be used as the device, but a device having a channel treated with a silane coupling agent is preferred.

Next, a solution containing the compound B is caused to flow through the channel of the device for a predetermined time. The solution containing the compound B can be prepared by dissolving the compound B in a solvent. Examples of the solvent include water, dichloromethane, methanol, acetone, methyl isobutyl ketone, toluene, propanol, and N-methylpyrrolidone. The solution flow conditions, which are not limited particularly, are as follows, for example: the pressure is 0.001 to 1 MPa, and preferably 0.005 to 0.1 MPa; and the solution flow time is 0.5 to 24 hours, and preferably 1 to 6 hours. Subsequently, the channel is subjected to a drying treatment so that the solvent is evaporated and removed, whereby the modification groups B are immobilized on the inner wall surface of the channel. The drying treatment can be carried out by, for example, introducing $N_2$ gas, Ar gas, or the like. The drying conditions are as follows, for example, though the drying conditions are not limited particularly as long as the compound B is immobilized to the inner wall surface and the solvent is removed: the pressure is, for example, 0.001 to 1 MPa, and preferably 0.005 to 0.1 MPa; the temperature is, for example, 15 to 150° C., and preferably 25 to 110° C.; and the time is, for example, 0.5 to 24 hours, and preferably 1 to 6 hours.

Then, a solution containing the compound A is caused to flow for a predetermined time through the channel to which the modification groups B are immobilized, which is followed by a drying treatment intended to evaporate and remove the solvent. As a result, the modification groups A are immobilized to the inner wall surface of the channel to which the modification groups B have been immobilized. The solvent dissolving the compound A, the solution flow conditions, and the drying conditions are identical to those for the compound B.

Washing and drying treatments are preferably carried out between the immobilization of the modification groups B and the immobilization of the modification groups A, and/or after the immobilization of the modification groups A. The washing treatment can be carried out by, for example, causing an organic solvent to flow through the channel. The conditions for this are not limited particularly.

Embodiment 1 has been explained so far with reference to an exemplary case where the modification groups A and B are introduced to the inner wall surface of the channel, but the present disclosure is not limited to this. In any one of the case where the modification group C and the modification group A are used, the case where the modification group C and the modification group B are used, and the case where the modification group C, the modification group A, and the modification group B are used, the modification of the inner wall surface can be achieved through the same operations as those for the case where the modification group B and the modification group A are used.

Embodiment 2

The following description explains Embodiment 2 as one embodiment of the substrate modification method of the present disclosure, by referring to an example in which a resin is used for forming the substrate.

First, a device having a channel is prepared.

In the case where a resin is used for forming the device, it is difficult in some cases to use an organic solvent such as dichloromethane, methanol, or acetone as a solvent. In such a case, in order to cause a silane coupling agent to be bound thereto, the channel is subjected to, in addition to the simple contact with the silane coupling agent, a surface treatment with vacuum ultraviolet rays VUV, or plasma so that carboxyl groups, hydroxyl groups, or aldehyde groups are generated, whereby the silane coupling agent can be bound thereto easily.

Further, when modification groups are introduced, it is also difficult to use an organic solvent in some cases. In this case, modification groups can be introduced directly to a resin surface, or on the silane coupling agent on a resin surface or the like, by using an aqueous catalytic reagent. In the case where aminosilane is bound to the resin, if the modification groups have carboxyl groups, the modification groups can be introduced by causing amide bonds to be formed by an aqueous catalyst such as DMT-MM (4-(4,6-dimethoxy-1,3,5-triazin-2-yl)-4-methylmorpholinium chloride n-hydrate) or WSC (water soluble carbodiimide, 1-ethyl-3-(3-dimethylaminopropyl)carbodiimide, hydrochloride). This treatment can be completed for 10 minutes to several hours, under the condition of room temperature to about 60° C. In the case where such a catalyst is used, the channel is desirably washed well with purified water or the like, so that the catalyst is removed completely after the introduction of modification groups.

Embodiment 3

The following description explains one embodiment of the electrophoresis method of the present disclosure as Embodiment 3, while referring to an exemplary case where capillary electrophoresis is used.

First, a running buffer is filled in a channel of a device. The filling of the running buffer can be carried out by applying pressure, using capillarity, or the like. Alternatively, a device having a channel in which a running buffer is filled preliminarily may be used. The running buffer can be decided appropriately depending on, for example, the type of the sample and the target analyte.

Next, a sample is introduced to one of apertures formed in the channel, and a voltage is applied across electrodes provided at apertures positioned on both ends of the channel. This causes the sample to migrate from the aperture through which the sample is introduced toward the other aperture. The voltage applied across the ends of the channel is not limited particularly, but can be decided appropriately depending on the sample, the target analyte, the running buffer, and the like. The voltage is, for example, 0.5 to 10 kV, and preferably 0.5 to 5 kV.

As the running buffer, a running buffer containing an anionic polymer may be used. In this case, the cathodic polymer in the running buffer is electrically coupled with a substance having a positive charge in the sample. Therefore, even if a difference regarding positive charge between substances contained in the sample is small, the substances can be separated and analyzed. In this case, the substance resulting from the coupling of the substance having the positive charge and the cathodic polymer has a negative charge. Therefore, it is preferable to cause an electroosmotic flow to be generated in a direction from a positive electrode toward a negative electrode in the channel. This embodiment can be preferably applied to measurement in the case where a target analyte is HbA1c. In the case where the target analyte is HbA1c, the cathodic polymer is, for example, preferably a cathodic group-containing polysaccharide, a cathodic group-containing acrylic polymer, or the like, more preferably, a carboxyl group-containing polysaccharide, a sulfonic group-containing polysaccharide, a carboxyl group-containing acrylic polymer, or a sulfonic group-containing acrylic polymer, though it is not limited particularly.

Then, the device is positioned at a predetermined site, and measurement is carried out. The measurement can be carried out by, for example, an optical technique. Examples of the optical technique include absorbance measurement, transmittance measurement, reflectance measurement, fluorometry and the like. The measurement wavelength can be determined appropriately in accordance with the sample, the target analyte and the like The present disclosure relates to one or a plurality of embodiments shown below:

[1] A substrate modification method including immobilizing, to a substrate surface, at least two types of modification groups selected from three types of modification groups that are a type of a modification group having one functional group, a type of a modification group having two to nine functional groups, and a type of a modification group having ten or more functional groups.

[2] A substrate modification method including immobilizing, to a substrate surface, a modification group having one functional group and a modification group having two to nine functional groups; a modification group having one functional group and a modification group having ten or more functional groups; a modification group having two to nine functional group and a modification group having ten or more functional groups; or a modification group having one functional group, a modification group having two to nine functional groups, and a modification group having ten or more functional groups.

[3] The substrate modification method according to [1] or [2], wherein the immobilization of the modification groups includes bringing at least two types of compounds into contact with a substrate surface, the at least two types of compounds being selected from three types of compounds that are a compound A having two functional groups; a compound B having three to ten functional groups; and a compound C having eleven or more functional groups.

[4] The substrate modification method according to [3],
wherein the compound A has one functional group to function as a part of the modification group and another functional group to be bound to the substrate surface; and/or
the compound B has two to nine functional groups to function as a part of the modification group and another functional group(s) to be bound to the substrate surface; and/or
the compound C has ten or more functional group to function as a part of the modification group and another functional group(s) to be bound to the substrate surface.

[5] The substrate modification method according to [3] or [4],
wherein the immobilization of the modification groups includes:
(1) bringing the compound B into contact with the substrate surface, and bringing the compound A into contact with the substrate surface that has been brought into contact with the compound B; or
(2) bringing the compound C into contact with the substrate surface, and bringing the compound B and/or the compound A into contact with the substrate surface that has been brought into contact with the compound C.

[6] A substrate modification method including immobilizing a modification group having one functional group, and a modification group having two or more functional groups, to a substrate surface.

[7] The substrate modification method according to [6],
wherein the immobilization of modification groups includes bringing the compound A having two functional groups and a compound B' having three or more functional groups into contact with the substrate surface.

[8] The substrate modification method according to [7],
wherein the compound A has one functional group to function as a part of the modification group, and a functional group(s) to be bound to the substrate surface, and/or
the compound B' has two or more functional group to function as a part of the modification group, and a functional group(s) to be bound to the substrate surface.

[9] The substrate modification method according to [7] or [8],
wherein the immobilization of the modification groups includes bringing the compound B' into contact with the substrate surface, and bringing the compound A into contact with the substrate surface that has been brought into contact with the compound B'.

[10] The substrate modification method according to any one of [1] to [9], wherein the substrate surface to which the modification groups are immobilized is treated with a silane coupling agent.

[11] The substrate modification method according to any one of [1] to [10], wherein the functional group is a polar group.

[12] The substrate modification method according to [11], wherein the polar group is selected from the group consisting of a carboxyl group, a sulfonic group, and an amino group.

[13] The substrate modification method according to any one of [2] to [5] and [7] to [12],
wherein the compound A is selected from the group consisting of dicarboxylic acid, monoaminocarboxylic acid, diamine, and monoaminosulfonic acid, and
the compound B or B' is selected from the group consisting of tetracarboxylic acid, hexacarboxylic acid, monoaminodicarboxylic acid, and disulfobenzoic acid.

[14] The substrate modification method according to any one of [1] to [13], wherein a material of the substrate is a resin, quartz, or glass.

[15] A method for manufacturing a separation analysis device having a channel, the method comprising immobilizing, to an inner wall surface of the channel, at least two types of modification groups selected from three types of modification groups that are a type of a modification group having one functional group, a type of a modification group having two to nine functional groups, and a type of a modification group having ten or more functional groups.

[16] A method for manufacturing a separation analysis device having a channel, the method including immobilizing, to an inner wall surface of the channel:
a modification group having one functional group, and a modification group having two to nine functional groups;
a modification group having one functional group, and a modification group having ten or more functional groups;
a modification group having two to nine functional groups, and a modification group having ten or more functional groups; or
a modification group having one functional group, a modification group having two to nine functional groups, and a modification group having ten or more functional groups.

[17] The method according to [15] or [16], wherein the immobilization of the modification groups includes bringing at least two types of compounds into contact with the substrate surface, the at least two types of compounds being selected from three types of compounds that are a compound A having two functional groups, a compound B having three to ten functional groups, and a compound C having eleven or more functional groups.

[18] The method according to [17],
wherein the compound A has one functional group to function as a part of the modification group, and a functional group to be bound to the substrate surface; and/or
the compound B has two to nine functional groups to function as a part of the modification group, and a functional group(s) to be bound to the substrate surface; and/or
the compound C has ten or more functional group to function as a part of the modification group, and a functional group(s) to be bound to the substrate surface.

[19] The method according to [17] or [18],
wherein the immobilization of the modification groups includes:
(1) bringing the compound B into contact with the substrate surface, and bringing the compound A into contact with the substrate surface that has been brought into contact with the compound B; or
(2) bringing the compound C into contact with the substrate surface, and bringing the compound B and/or the compound A into contact with the substrate surface that has been brought into contact with the compound C.

[20] A method for manufacturing a separation analysis device having a channel, the method including immobilizing a modification group having one functional group, and a modification group having two or more functional groups, to an inner wall surface of the channel.

[21] The method according to [20], wherein the immobilization of the modification groups includes bringing a compound A having two functional groups, and a compound B' having three or more functional groups into contact with the inner wall surface of the channel.

[22] The method according to [21],
wherein the compound A has one functional group to function as a part of the modification group, and a functional group to be bound to the inner wall surface of the channel, and/or
the compound B' has two or more functional group to function as a part of the modification group, and a functional group to be bound to the inner wall surface of the channel.

[23] The method according to [21] or [22],
wherein the immobilization of the modification groups includes bringing the compound B' into contact with the inner wall surface of the channel, and bringing the compound A into contact with the inner wall surface of the channel that has been brought into contact with the compound B'.

[24] The method according to any one of [15] to [23], wherein the substrate surface or the inner wall surface of the channel to which the modification groups are immobilized is treated with a silane coupling agent.

[25] The method according to any one of [15] to [24], wherein the functional group is a polar group.

[26] The substrate modification method according to [25], wherein the polar group is selected from the group consisting of a carboxyl group, a sulfonic group, and an amino group.

[27] The substrate modification method according to any one of [17] to [19] and [21] to [26],
wherein the compound A is selected from the group consisting of dicarboxylic acid, monoaminocarboxylic acid, diamine, and monoaminosulfonic acid, and
the compound B or B' is selected from the group consisting of tetracarboxylic acid, hexacarboxylic acid, monoaminodicarboxylic acid, and disulfobenzoic acid.

[28] The substrate modification method according to any one of [15] to [27], wherein a material of the substrate or the inner wall of the channel is a resin, quartz, or glass.

[29] A separation analysis device having a channel, wherein at least two types of modification groups selected from three types of modification groups that are a type of a modification group having one functional group, a type of a modification group having two to nine functional groups, a type of a modification group having ten or more functional groups are immobilized to an inner wall surface of the channel.

[30] The separation analysis device according to [29], wherein the modification group having one functional group, the modification group having two to nine functional group, and the modification group having ten or more functional groups, are immobilized to the inner wall surface of the channel via a silane coupling agent.

[31] A separation analysis device having a channel, wherein a modification group having one functional group, and a modification group having two or more functional groups, are immobilized to an inner wall surface of the channel.

[32] The separation analysis device according to [31], wherein the modification group having one functional group and the modification group having two or more functional groups are immobilized to the inner wall surface of the channel via a silane coupling agent.

[33] The separation analysis device according to any one of [29] to [32], the separation analysis device being a capillary tube, or an electrophoresis chip.

[34] A method for performing capillary electrophoresis, using the separation analysis device according to any one of [29] to [33].

Hereinafter the present disclosure is further explained with reference to Examples and Comparative Examples. For the interpretation, however, the present invention is not limited to Examples shown below.

EXAMPLE

Example 1

A capillary tube having an inner wall modified by a compound having two functional groups and a compound having four functional groups (a capillary tube having an inner wall surface immobilized the modification groups having one functional group and the modification groups having three functional groups) was produced.

[Treatment with Anchor Compound]

A capillary tube (made of fused silica glass, total length: 320 mm, effective length: 85 mm, inner diameter: 50 μm) was prepared, and an inner wall of the capillary tube was treated through the following procedure with an anchor compound (3-aminopropyltrimethoxy silane), whereby the inner wall of the capillary tube was modified with amino silane. First, 1N—NaOH was caused to flow through the capillary tube at 0.1 MPa for 1 hour, and ion exchange water was caused to flow therethrough at 0.1 MPa for 15 minutes. Thereafter, $N_2$ gas was introduced at 0.1 MPa, at 110° C., for 1 hour. Then, a 5% aqueous solution of 3-aminopropyltrimethoxy silane was caused to flow therethrough at 0.1 MPa for 1 hour, $N_2$ gas was introduced at 0.1 MPa for 3 minutes, and thereafter both ends of the capillary tube were fused and sealed with use of an oxygen-mixed gas burner. The capillary tube was heated at 110° C. for 6 hours. Then, the fused and sealed ends of the capillary tube were opened, $N_2$ gas was introduced at 0.1 MPa for 20 minutes, and thereafter, dichloromethane, methanol, and ion exchange water were caused to flow through the capillary tube in the stated order at 0.1 MPa for 20 minutes each. Then, $N_2$ gas was introduced at 0.1 MPa, at 50° C., for 1 hour.

[Treatment with Compound Having Two Functional Groups and Compound Having Four Functional Groups]

First, 0.1 mol/L pyromellitic dianhydride solution (molecular weight: 218.12, solvent: N-methylpyrrolidone) was caused to flow through a capillary tube having an inner wall modified with aminosilane, at 0.1 MPa for 1 hour, and after being kept for 1 hour, it was caused to flow further for 1 hour at 0.005 MPa. Subsequently, $N_2$ gas was introduced at 0.1 MPa at 50° C. for 1 hour, and thereafter, N-methylpyrrolidone was caused to flow therethrough at 0.1 MPa for 30 minutes, methanol was caused to flow therethrough at 0.1 MPa for 30 minutes, and then, $N_2$ gas was introduced at 0.1 MPa at 50° C. for 30 minutes, whereby washing and drying was carried out. Next, 0.1 mol/L succinic anhydride solution (molecular weight: 100.07, solvent: N-methylpyrrolidone) was caused to flow at 0.1 MPa, and after being kept for 1 hour, it was caused to flow further for 1 hour at 0.005 MPa. Subsequently, $N_2$ gas was introduced at 0.1 MPa at 50° C. for 1 hour, and thereafter, N-methylpyrrolidone was caused to flow therethrough at 0.1 MPa for 30 minutes, methanol was caused to flow therethrough at 0.1 MPa for 30 minutes, and then, $N_2$ was introduced at 0.1 MPa for 50° C. for 30 minutes, whereby washing and drying was carried out. Then, a running buffer was caused to flow at 0.1 MPa for 10 minutes, ion exchange water was caused to flow at 0.1 MPa for 10 minutes, and thereafter, $N_2$ gas was introduced at 0.1 MPa at 50° C. for 1 hour.

Comparative Example 1

A capillary tube was produced in the same manner as that of Example 1 except that the treatment with pyromellitic dianhydride solution and washing and drying subsequent to the foregoing treatment were not carried out. In other words, in Comparative Example 1, the inner wall of the capillary tube modified with aminosilane was only subjected to the treatment with succinic anhydride solution (a compound having two functional groups).

Comparative Example 2

A capillary tube was produced in the same manner as that of Example 1 except that the treatment with succinic anhydride solution and the washing and drying subsequent to the foregoing treatment were not carried out. In other words, in Comparative Example 2, the inner wall of the capillary tube modified with aminosilane was only subjected to the treatment with pyromellitic dianhydride solution (a compound having four functional groups).

[Evaluation of Capillary Tube]

Measurement was carried out with use of the capillary tubes produced in Example 1, Comparative Examples 1 and 2 under the following conditions, and EOF rates and states of separation of hemoglobin components (peak width, peak detection time) of the respective capillary tubes were evaluated.

Figure 1B:
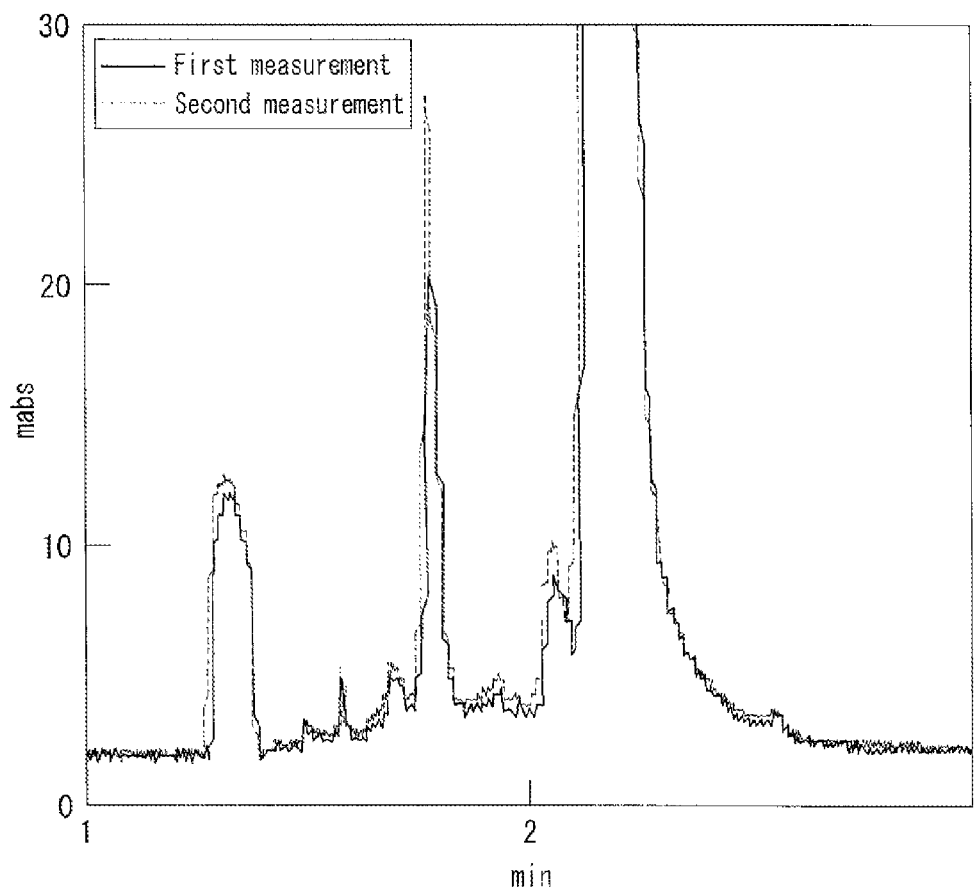
Figure 2A:
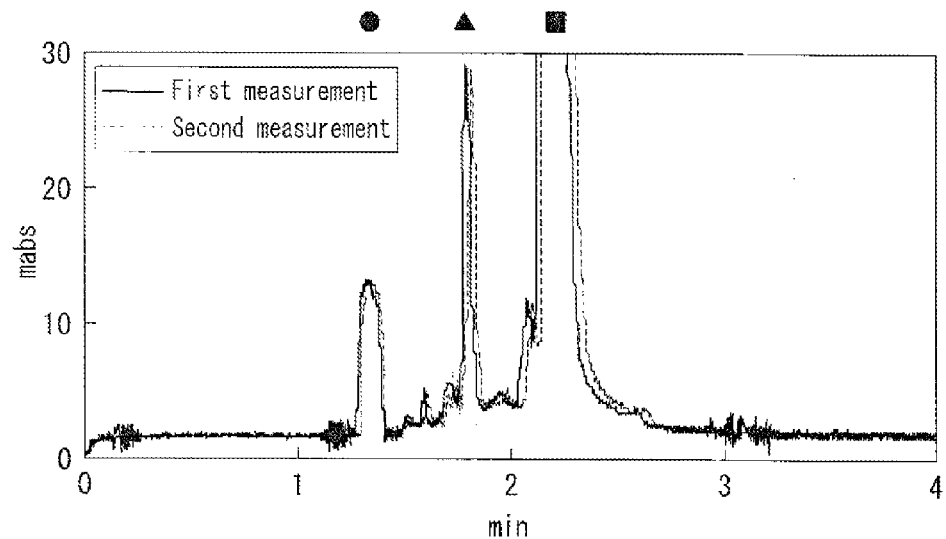
FIGS. 2A and 2B are graphs showing the exemplary results of Comparative Example 1.
Figure 2B:
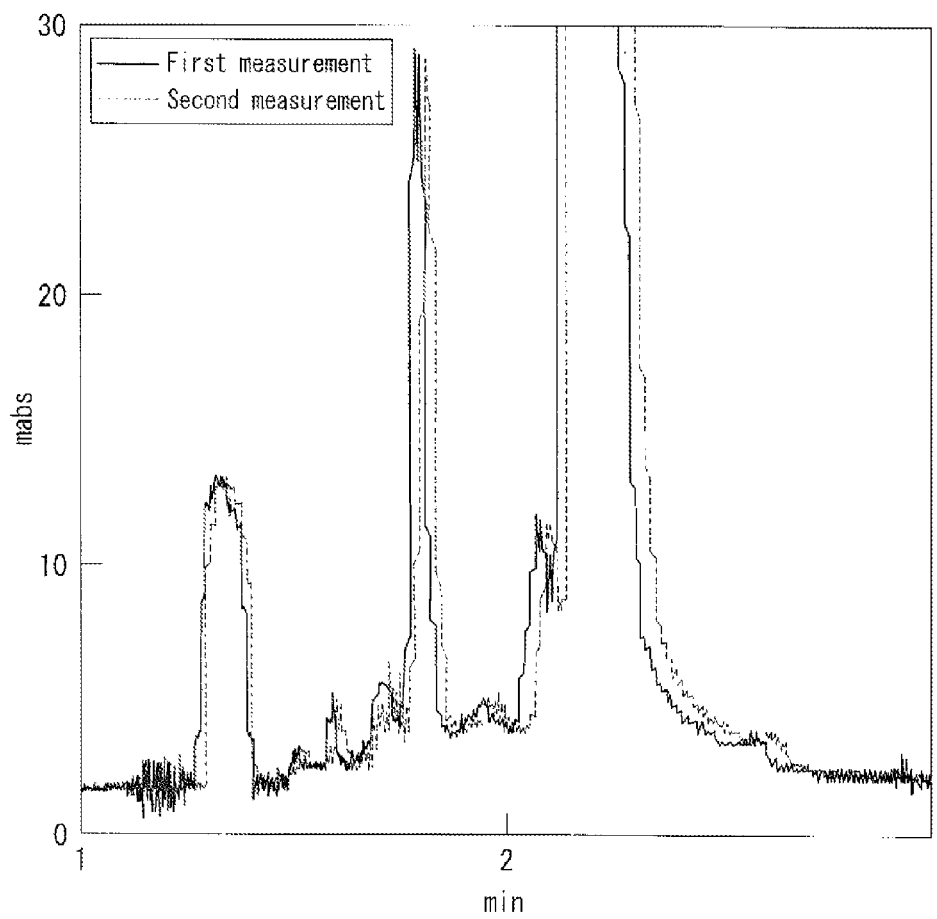
Figure 3A:
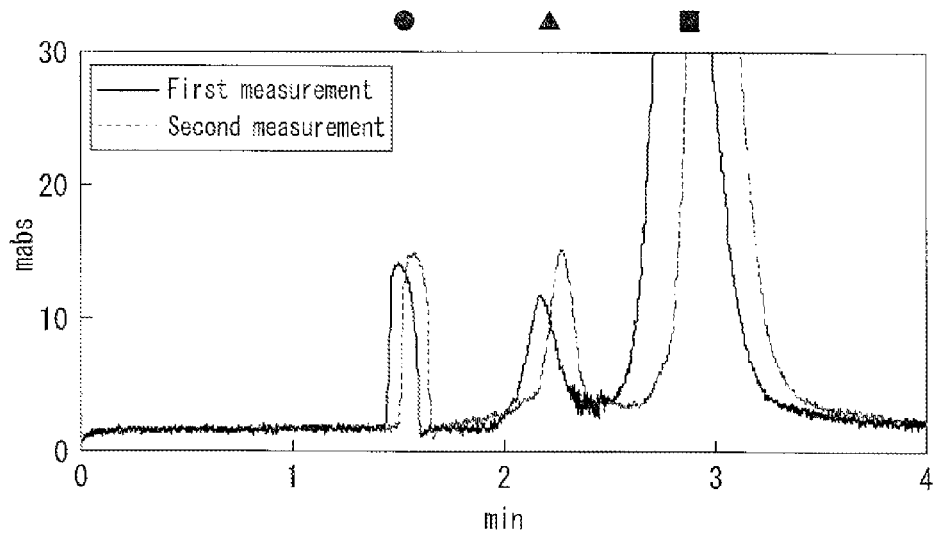
FIGS. 3A and 3B are graphs showing the exemplary results of Comparative Example 2.
Figure 3B:
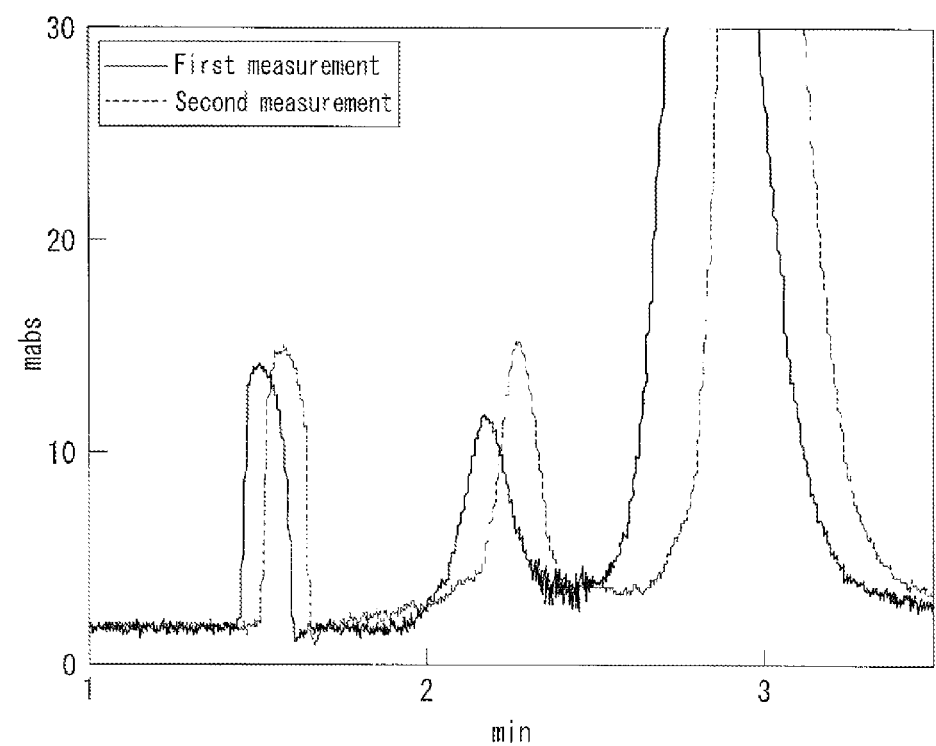

[Measurement Condition]
Device: CE device manufactured by Agilent
Separation length: 8.5 cm (total length: 32 cm)
Voltage: 12.8 kV (400 V/cm)
Migration solution: 100 mM of L-tartaric acid-arginine-(pH 4.9) (containing 0.8% of sodium chondroitin sulfate C and 2 mM of CyDTA)
Sample: freeze-dried hemoglobin dissolved in distilled water (hemoglobin concentration: about 5 g/L)
Sample introduction method: partial introduction by pressure method (50 mbar, 5 sec)
Measurement method: a running buffer is caused to flow (2 minutes)→pre-energization (1 minute)→sample introduction→measurement Results obtained by the above-described measurement operations are shown in Table 1 below and FIGS. 1 to 3. FIGS. 1 to 3 are graphs showing variations of absorbances, which are obtained by processing obtained electropherograms. FIG. 1 shows results of Example 1, FIG. 2 shows results of Comparative Example 1, and FIG. 3 shows results of Comparative Example 2. In FIGS. 1 to 3, a peak indicated by a circle in the upper part is a peak of EOF, a peak indicated by a triangle is a peak of HbA1c, and a peak indicated by a square is a peak of HbA0. (b) is a partial enlarged view of (a).

TABLE 1

| | | First measurement operation | Second measurement operation | Difference (first − second) |
|---|---|---|---|---|
| Ex. 1 | EOF | 79.4 sec | 79.2 sec | 0.2 sec |
| | HbA1c | 106.9 sec | 106.7 sec | 0.2 sec |
| | HbA0 | 129.5 sec | 128.5 sec | 1.0 sec |
| Comp. Ex. 1 | EOF | 79.3 sec | 80.6 sec | 1.3 sec |
| | HbA1c | 107.3 sec | 108.7 sec | 1.4 sec |
| | HbA0 | 128.8 sec | 130.7 sec | 1.9 sec |
| Comp. Ex. 2 | EOF | 90.4 sec | 94.5 sec | 4.1 sec |
| | HbA1c | 130.3 sec | 136.5 sec | 6.2 sec |
| | HbA0 | 169.7 sec | 177.6 sec | 7.9 sec |

As to the capillary tube of Example 1, EOF was observed at 79.3 seconds in average, as shown in Table 1 and FIG. 1. Thus, excellent results, such as the EOF rate of 1.1 mm/sec, was exhibited. As shown in FIG. 1, the half value width thereof was 1.8 mm, which is narrow. Thus, excellent resolution was exhibited with respect to the hemoglobin components. Further, as shown in Table 1 and FIG. 1, substantially no difference was seen between the first measurement operation and the second measurement operation regarding the EOF rate, and the peak detection times of the hemoglobin components. This proves that separation was carried out with excellent reproducibility. Peaks immediately before and after the peak of hemoglobin A1c were separately detected as peaks, and peaks immediately before and after the peak of hemoglobin A0 were also separately detected as peaks. Therefore, it was confirmed that the capillary tube of Example 1 had a surface state that enabled a high EOF rate, and excellent separation with excellent reproducibility.

On the other hand, as to the capillary tube of Comparative Example 1, which had been subjected only to treatment with the succinic anhydride solution, EOF was observed at 79.3 seconds in the first measurement operation and at 80.6 seconds in the second measurement operation. Thus, excellent results, such as the EOF rate of 1.1 mm/sec, was exhibited. The half value width thereof, however, was 2.1 mm, which means that resolution with respect to the hemoglobin components was low as compared with Example 1. Further, the difference between the first measurement operation and the second measurement operation regarding the EOF rate, and the peak detection times of the hemoglobin components were greater, as compared with Example 1. In the capillary tube of Comparative Example 2, which had been subjected only to the treatment with pyromellitic dianhydride solution, adsorption of a large amount of Hb occurred at the beginning in the first measurement operation, and a peak of hemoglobin, which should have appeared before, and in the vicinity of, the peak of HbA1c was not detected. It should be noted that this adsorption of Hb was suppressed in the second measurement operation. However, the peaks of hemoglobin A1a and hemoglobin A1b, which should have been detected first, were not detected as peaks. Peaks immediately before and after the peak of hemoglobin A1c were not detected as peaks, but were integrated with the peak of hemoglobin A1c in the detection, and peaks immediately before and after the peak of hemoglobin A0 were also not detected as peaks, but were integrated with the peak of hemoglobin A0 in the detection. EOF was observed at 90.4 seconds in the first measurement operation and at 94.5 seconds in the second measurement operation. The EOF rate was 0.9 mm/sec, which is slow, and the half value width thereof was 7.0 mm. Thus, the resolution with respect to the hemoglobin components was significantly low, as compared with Example 1. Further, differences between the first measurement operation and the second measurement operation regarding the EOF rate, and the peak detection times of the hemoglobin components were great, as compared with Example 1.

Example 2

A chip made of resin, having a channel with an inner wall surface modified by a compound having two functional groups and a compound having ten or more functional groups, (a chip having channel with an inner wall surface immobilized the modification groups having one functional group and the modification groups having three functional groups) was produced.
[Production of Resin Chip]

Figure 4:
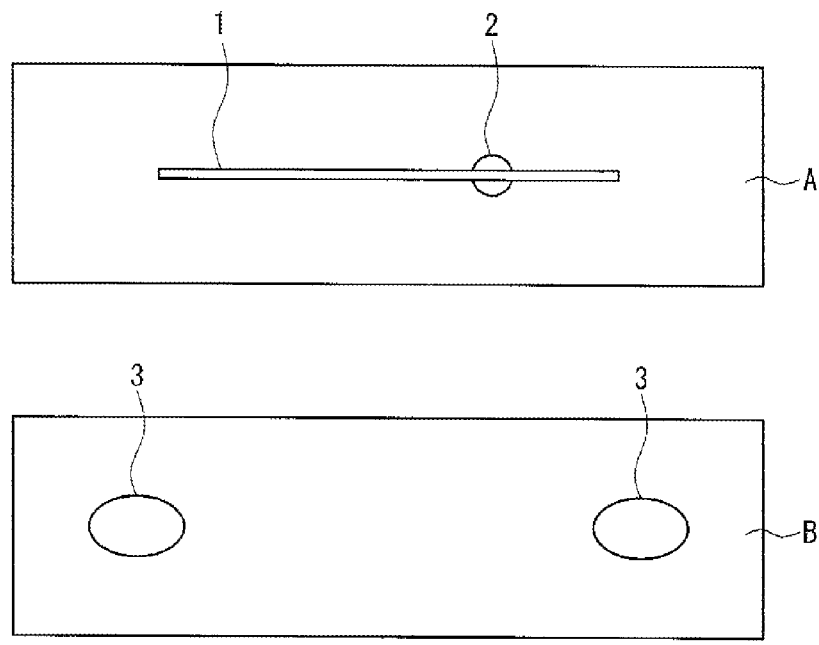
FIG. 4 is a top view of a resin plate used in a device of Example 2.

A resin plate A made of methyl polymethacrylate resin, having a separation channel 1 and a detection window 2, and a resin plate B made of methyl polymethacrylate resin, having two through holes (a sample vial and a running buffer vial), as shown in FIG. 4, were prepared. A surface of the resin plate A on which the channel was formed, and a surface of the resin plate B to be bonded to the resin plate A, were treated with ultraviolet rays (VUV), and functional groups such as carboxylic groups were introduced on either surface of each of the resin plates A and B. The resin plates A and B having been subjected to VUV were immersed in 5% aqueous solution of 3-aminopropyltrimethoxy silane at 30° C. for 3 hours, and thereafter, an extra portion of 3-aminopropyltrimethoxy silane was removed by purified water. The resin plates were dried in a vacuum dryer at 45° C. for 1 hour, whereby the aminosilane-treated resin plates A and B were obtained.
[Treatment with Compound Having Two Functional Groups and Compound Having Ten or More Functional Groups]

First, the aminosilane-treated resin plates A and B were immersed in 0.5 M hydrochloric acid for 10 minutes, and were washed with purified water. Thereafter, the plates were immersed in a treatment solution containing 1% of chondroitin sulfate C (Seikagaku Corporation, molecular weight: 40,000 to 80,000, the number of functional groups: about 80 to 160) and 10 mM of DMT-MM for 4 hours, and further, immersed in a treatment solution containing 100 mM of succinic acid and 10 mM of DMT-MM at room temperature for 4 hours, whereby chondroitin sulfate and succinic acid were introduced to surfaces of the aminosilane-treated resin plates. The resin plates to which chondroitin sulfate and succinic acid were introduced were washed sufficiently with sodium hydrochloride, hydrochloric acid, and purified water, and were dried in a vacuum dryer at 45° C. for 1 hour. The surface of the resin plate A where the channel was formed and the surface of the resin plate B to be bonded with the resin plate A were applied to each other, and were heated and pressed, whereby the resin plates A and B were bonded to each other. Thus, a resin chip (device) to which chondroitin sulfate and succinic acid were introduced was obtained.

Comparative Example 3

A resin chip was produced in the same manner as that of Example 2 except for that the immersion in the treatment solution containing 1% of chondroitin sulfate C and 10 mM of DMT-MM at room temperature for 4 hours was not carried out. In other words, in Comparative Example 3, only the treatment with succinic acid (chemical compound having two functional groups) was carried out, whereby a succinic acid-introduced resin chip was obtained.

Comparative Example 4

A resin chip was produced in the same manner as that of Example 2 except for that the immersion in the treatment solution containing 100 mM of succinic acid and 10 mM of DMT-MM at room temperature for 4 hours was not carried out. In other words, in Comparative Example 4, only the treatment with chondroitin sulfate (chemical compound having ten or more functional groups) was carried out, whereby a chondroitin sulfate-introduced resin chip was obtained.
[Evaluation of Resin Chip]

Measurement was carried out with use of the resin chips produced in Example 2, Comparative Examples 3 and 4 under the following conditions, and EOF rates and states of separation of hemoglobin components (peak width, peak detection time) of the respective resin chips were evaluated. In the measurement, after a running buffer was filled in the separation channel and the running buffer vial and a hemoglobin sample solution was filled in the sample vial, a voltage of 600 V/cm was applied, so that hemoglobin was measured.
[Measurement Condition]
Device: an electrophoresis measurement device produced by the inventor was used.
Separation length: 20 cm
Voltage: 1800 kV (600 V/cm)
Migration solution: 40 mM of citric acid (pH 5.3) (1% sodium chondroitin sulfate)
Sample: control material for hemoglobin A1c diluted with the running buffer (hemoglobin concentration: 5 g/L)

The resin chips of Example 2, Comparative Example 3, and Comparative Example 4 exhibited EOF rates of 2.2 mm/sec, 0.7 mm/sec, and 1.8 mm/sec, respectively. The resin chip of Example 2, to which both of chondroitin sulfate (compound having ten or more functional groups) and succinic acid (compound having two functional group) were introduced, exhibited the fastest EOF rate, as compared with the resin chips of Comparative examples 3 and 4, to which either one of the compounds was introduced.

Figure 5:
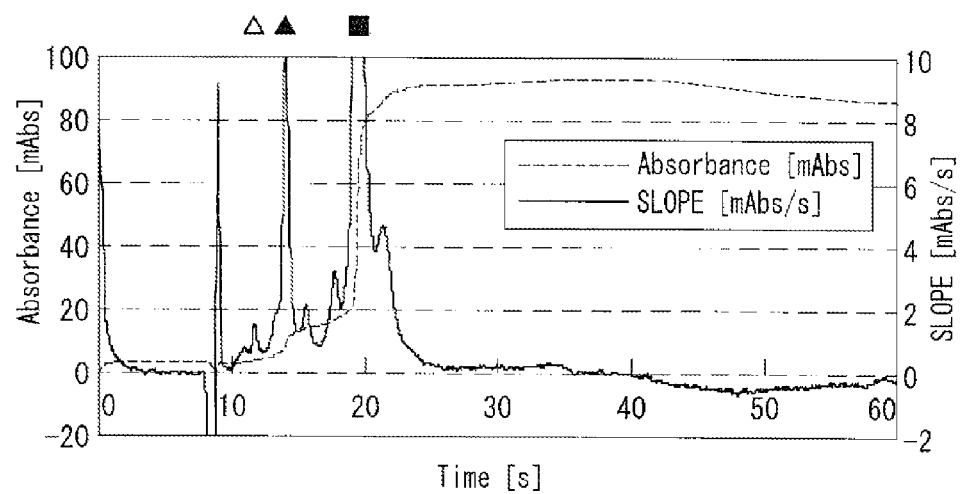
FIG. 5 is a graph showing the exemplary results of Example 2.
Figure 6:
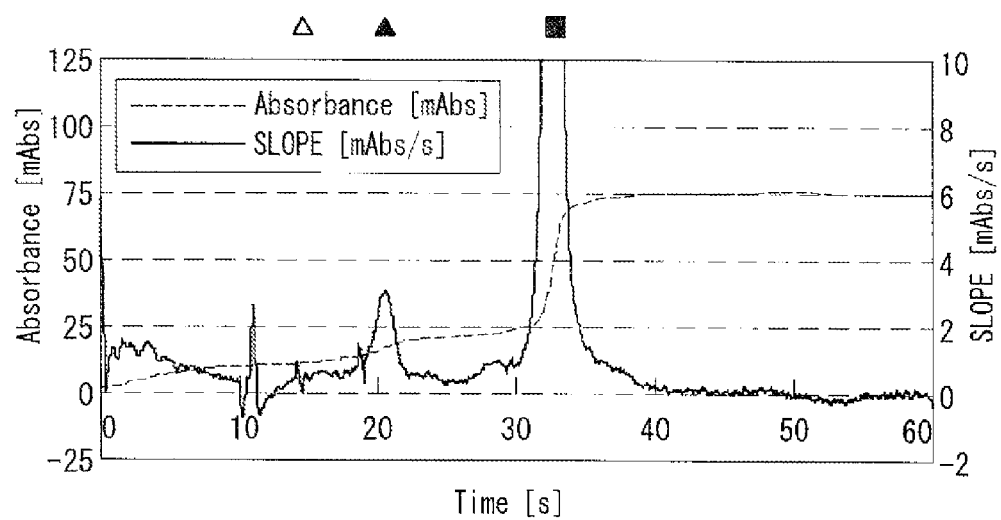
FIG. 6 is a graph showing the exemplary results of Comparative Example 4.

Results obtained by the above-described measurement are shown in FIGS. 5 and 6. FIGS. 5 and 6 are graphs showing variations of absorbances, which are obtained by processing obtained electropherograms. FIG. 5 shows results of Example 2, and FIG. 6 shows results of Comparative Example 4. In FIGS. 5 and 6, a peak indicated by a triangle in the upper part is a peak of HbA1c, a peak indicated by a square is a peak of HbA0, and a peak of a void triangle is a peak of HbA1a or HbA1b.

As shown in FIG. 5, in the case of the resin chip of Example 2, the separation of hemoglobin was completed in 25 seconds, and every peak, such as the peak of hemoglobin A1c and the peak of hemoglobin A0, had a narrow width, and was sharp. The peak width of hemoglobin A1c was 1.4 mm (half value width: 0.65 mm), and peaks immediately before and after the peak of hemoglobin A1c could be detected separately as discrete, independent peaks. The peaks of hemoglobin A1a and hemoglobin A1b, which should be detected first, could be detected as independent peaks. Thus, highly accurate measurement was achieved. Besides, peaks immediately before and after the peak of hemoglobin A0 could be detected separately. Thus, highly accurate measurement was achieved.

In contrast, with the resin chip of Comparative Example 3, hemoglobin was not detected. The reasons for this can be assumed to be that hemoglobin non-specifically adsorbed to inside of the separation channel, and that hemoglobin was not migrated in the measurement time of 60 seconds, since the EOF rate was slow.

In the resin chip of Comparative Example 4, the separation of hemoglobin took 40 seconds, which was about 1.6 times the time in Example 2. Besides, peak widths of all types of hemoglobin were wider. The peak width of hemoglobin A1c was 2.8 mm (half value width: 1.3 mm), and peaks immediately before and after the peak of hemoglobin A1c were not detected as discrete, independent peaks and were integrated with the peak of hemoglobin A1c in detection. Besides, peaks of hemoglobin A1a and hemoglobin A1b, which should have been detected first, were not detected as peaks. Furthermore, peaks immediately before and after the peak of hemoglobin A0 were not detected as discrete, independent peaks and were integrated with the peak of hemoglobin A0 in detection. These results show that the measurement with use of the resin chip of Comparative Example 4 had poor accuracy.

The present disclosure is useful in fields of medical care, and/or academic fields such as medicine, biochemistry, and biology not aimed for medical care.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A separation analysis device comprising
a channel, wherein the channel is a part of a capillary tube or an electrophoresis chip,
wherein modification groups are immobilized, via a silane coupling agent, to an inner wall surface of the channel,
wherein the modification groups are a combination of a succinic group and a pyromellitic acid, or a combination of a succinic group and chondroitin sulfate.

2. The separation analysis device according to claim 1, wherein the chondroitin sulfate is selected from the group consisting of the following formulae

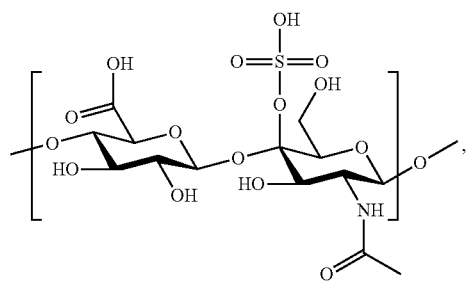

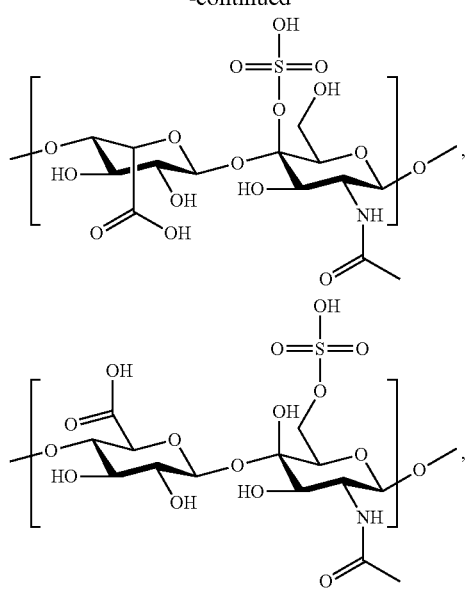

and combinations thereof.

3. The separation analysis device according to claim 1, wherein a material of the channel is selected from the group consisting of acrylic resins, polymethyl methacrylate, polycarbonate, polyvinylidene chloride, cyclic polyolefin, polyether ether ketone, polystyrene, polytetrafluoroethylene (PTFE), quartz, and glass.

4. A method for performing capillary electrophoresis, using the separation analysis device according to claim 1.

5. A substrate modification method comprising:
providing a substrate comprising a channel for capillary electrophoresis, wherein the channel is a part of a capillary tube or an electrophoresis chip,
immobilizing, to the substrate surface, via a silane coupling agent, a combination of a succinic group and a pyromellitic acid, or a combination of a succinic group and chondroitin sulfate.

6. A method for manufacturing a separation analysis device having a channel, wherein the channel is a part of a capillary tube or an electrophoresis chip, the method comprising immobilizing, to an inner wall surface of the channel, via a silane coupling agent, a combination of a succinic group and a pyromellitic acid, or a combination of a succinic group and chondroitin sulfate.

* * * * *